US011157596B1

(12) United States Patent
Eby et al.

(10) Patent No.: US 11,157,596 B1
(45) Date of Patent: Oct. 26, 2021

(54) SYSTEMS AND METHODS FOR AUTOMATICALLY ACCESSING PRESCRIPTION STATUS INFORMATION OVER A NETWORK IN RESPONSE TO SCANNING A BARCODE

(71) Applicant: WALGREEN CO., Deerfield, IL (US)

(72) Inventors: Nicholas L. Eby, Downers Grove, IL (US); Joseph M. Rago, Hinsdale, IL (US); Timothy P. McCauley, Evanston, IL (US)

(73) Assignee: WALGREEN CO., Deerfield, IL (US)

( * ) Notice: Subject to any disclaimer, the term of this patent is extended or adjusted under 35 U.S.C. 154(b) by 1217 days.

(21) Appl. No.: 14/697,725

(22) Filed: Apr. 28, 2015

(51) Int. Cl.
*G06F 19/00* (2018.01)

(52) U.S. Cl.
CPC ............................... *G06F 19/3456* (2013.01)

(58) Field of Classification Search
CPC .... G06F 19/00; G06F 19/3456; G06F 19/328; G06Q 50/22
See application file for complete search history.

(56) References Cited

U.S. PATENT DOCUMENTS

| | | | |
|---|---|---|---|
| 2004/0260577 A1* | 12/2004 | Dahlin et al. ........... | G06F 17/60 705/2 |
| 2005/0004700 A1* | 1/2005 | DiMaggio ................ | G06F 7/00 700/213 |
| 2005/0102163 A1* | 5/2005 | Coughlin ................ | G06F 17/60 705/2 |
| 2008/0222042 A1* | 9/2008 | Moore et al. ............. | H04L 9/32 705/55 |
| 2012/0185264 A1* | 7/2012 | Demogenes et al. ... | G06Q 50/00 705/2 |
| 2013/0110555 A1* | 5/2013 | Dunham et al. | |
| 2013/0218592 A1* | 8/2013 | Hashmat ................ | G06Q 50/24 705/3 |
| 2014/0330579 A1* | 11/2014 | Cashman et al. ....... | G06F 19/00 705/2 |
| 2015/0120321 A1* | 4/2015 | David et al. | |
| 2015/0161351 A1* | 6/2015 | Scalpati | |
| 2016/0103978 A1* | 4/2016 | Stong | |
| 2019/0163876 A1* | 5/2019 | Remme et al. | |

* cited by examiner

*Primary Examiner* — Michael Tomaszewski
*Assistant Examiner* — William T. Monticello
(74) *Attorney, Agent, or Firm* — Marshall, Gerstein & Borun LLP; Randall G. Rueth

(57) ABSTRACT

The methods and systems may allow a user to launch a client application on an internet-enabled device, and to subsequently navigate to an image capture screen within the client application. In response to receiving a command from a user, the client application may execute a barcode scanning routine to scan a barcode, and that decodes the barcode into prescription label data. Alternatively, the prescription label data may be manually entered by a user. The automatic data access methods and systems may automatically retrieve prescription status data according to the prescription label data. The prescription status data may be indicative of a prescription from a first pharmacy, a prescription from a second pharmacy, or a prescription that has already been filled. The methods and systems either automatically refills the prescription, automatically generates a prescription transfer request, or automatically generates a prescription already filled message, based on the prescription status data.

20 Claims, 25 Drawing Sheets

SYSTEMS AND METHODS FOR AUTOMATICALLY ACCESSING PRESCRIPTION STATUS INFORMATION OVER A NETWORK IN RESPONSE TO SCANNING A BARCODE

TECHNICAL FIELD

The present disclosure generally relates to systems and methods for accessing prescription status information. More particularly, the present disclosure relates to methods and systems for automatically accessing prescription status information in response to receiving prescription label number data.

BACKGROUND

Currently, an individual seeking to access prescription status information (e.g., prescription pending for refill, prescription already refilled, an associated pharmacy, etc.) needs to know a lot about the associated prescription. For example, the individual needs to know whether the prescription has already been refilled, what pharmacy the prescription is with, what the prescription is for, etc. A prescription label number may be associated with this prescription information.

Barcodes are widely used in a variety of automatic identification and data capture systems including identifying retail products at a grocery store or a department store, verifying an identity of airline passengers, keying a medical record or a medication to a patient, tracking parcels for a mail carrier, and automatically accessing a webpage. Moreover, barcodes may encode data or messages using one of a wide assortment of symbologies, such as one-dimensional linear barcodes (e.g., Universal Product Code (UPC), Code 128, ITF-14, prescription barcodes, etc.) or two-dimensional matrix barcodes (e.g., Quick Response Code (QR Code), Data Matrix, MaxiCode, Aztec Code, etc.). Each symbology incorporates its own unique mapping between a message and a barcode; the mapping encodes both the digits and/or the characters of the message and start and stop markers into a symbols (e.g., bars, rectangles, dots, hexagons, etc.) and spaces.

Generally, a particular type of barcode is designed for and used in a particular application. For example, the UPC barcode was originally designed for an automated checkout system at a supermarket and now has expanded to uniquely encode all types of retail products. The two-dimensional QR Code barcode is designed to encode a relatively large amount of data and is used, for example, to encode a message or a link to a webpage for a user. Additionally, pharmacies have adopted specific types of barcodes for keying unique prescription number to a specific medical prescription and have affixed prescription barcodes to prescription bottles and/or packaging. More recently, barcode interpretive software has become available for smartphones that allow a user to scan a barcode via a camera built into the smartphone.

Convenient mechanisms are needed for individuals to access prescription status information.

SUMMARY

A system for dynamically accessing prescription status data may include a prescription label data receiving module stored on a memory that, when executed by a processor, causes the processor to receive prescription label data. The system may further include a prescription status data receiving module stored on a memory that, when executed by a processor, causes the processor to automatically receive prescription status data, from a remote computing device, based on the prescription label data, wherein the prescription status data is representative of a status of a prescription. If the status of the prescription is indicative of an existing prescription from a first pharmacy, the prescription is automatically filled by the first pharmacy. If the status of the prescription is indicative of an existing prescription from a second pharmacy, a prescription transfer request is automatically initiated to transfer the prescription to the first pharmacy. If the status of the prescription is indicative of a prescription that has already been refilled, a message is automatically generated indicating that the prescription has already been refilled.

In another embodiment, a method for dynamically accessing prescription status data may include receiving prescription label data at a processor of a computing device in response to the processor of the computing device executing a prescription label data receiving module. The method may further include receiving prescription status data, at the processor of the computing device, from a remote computing device, based on the prescription label data in response to the processor of the computing device executing a prescription status data receiving module, wherein the prescription status data is representative of a status of a prescription. If the status of the prescription is indicative of an existing prescription from a first pharmacy, the prescription is automatically filled by the first pharmacy. If the status of the prescription is indicative of an existing prescription from a second pharmacy, a prescription transfer request is automatically initiated to transfer the prescription to the first pharmacy. If the status of the prescription is indicative of a prescription that has already been refilled, a message is automatically generated indicating that the prescription has already been refilled.

In a further embodiment, a non-transitory computer-readable medium storing instructions that, when executed by a processor of a computing device, cause the processor to dynamically access prescription status data may include a prescription label data receiving module that, when executed by a processor, causes the processor to receive prescription label data. The non-transitory computer-readable medium may further include a prescription status data receiving module that, when executed by a processor, causes the processor to automatically receive prescription status data, from a remote computing device, based on the prescription label data, wherein the prescription status data is representative of a status of a prescription. If the status of the prescription is indicative of an existing prescription from a first pharmacy, the prescription is automatically filled by the first pharmacy. If the status of the prescription is indicative of an existing prescription from a second pharmacy, a prescription transfer request is automatically initiated to transfer the prescription to the first pharmacy. If the status of the prescription is indicative of a prescription that has already been refilled, a message is automatically generated indicating that the prescription has already been refilled.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment of thereof. Further, wherever possible, the following description refers to the reference numerals included in the following figures, in which features depicted in multiple figures are designated with consistent reference numerals.

DETAILED DESCRIPTION

The methods and systems of the present disclosure may provide a single point of input, via a barcode scan or manual entry of a prescription label, in order to dynamically initiate automatic refill of a pending prescription, automatic generation of a prescription status message associated with a prescription, or automatic initiation of a prescription transfer request, to transfer an existing prescription from a second pharmacy to a first pharmacy, in response to receiving prescription label data.

Accordingly, memory and processing requirements, associated with related computing devices and systems, are reduced. For example, because a single point of input may be provided, associated computing devices may store a reduced number of user interface generation modules and, thus, may process a reduced number of user interface generation modules.

The methods and systems may, for example, allow a user to launch a client application on an internet-enabled device, and to navigate to an image capture screen within the client application to scan a barcode, or to navigate to a prescription label number input screen to manually enter a prescription label number. In response to receiving a command from a user, the client application may execute a barcode scanning routine to scan a barcode, and may decode the barcode into, for example, prescription label number data.

The automatic prescription status data access methods and systems of the present disclosure may automatically retrieve prescription status data according to the prescription label data. The prescription status data may be indicative of a prescription from a first pharmacy, a prescription from a second pharmacy, or a prescription that has already been filled. The methods and systems may either automatically refill the prescription, automatically generate a prescription transfer request, or automatically generate a prescription already filled message, based on the prescription status data.

Figure 1:
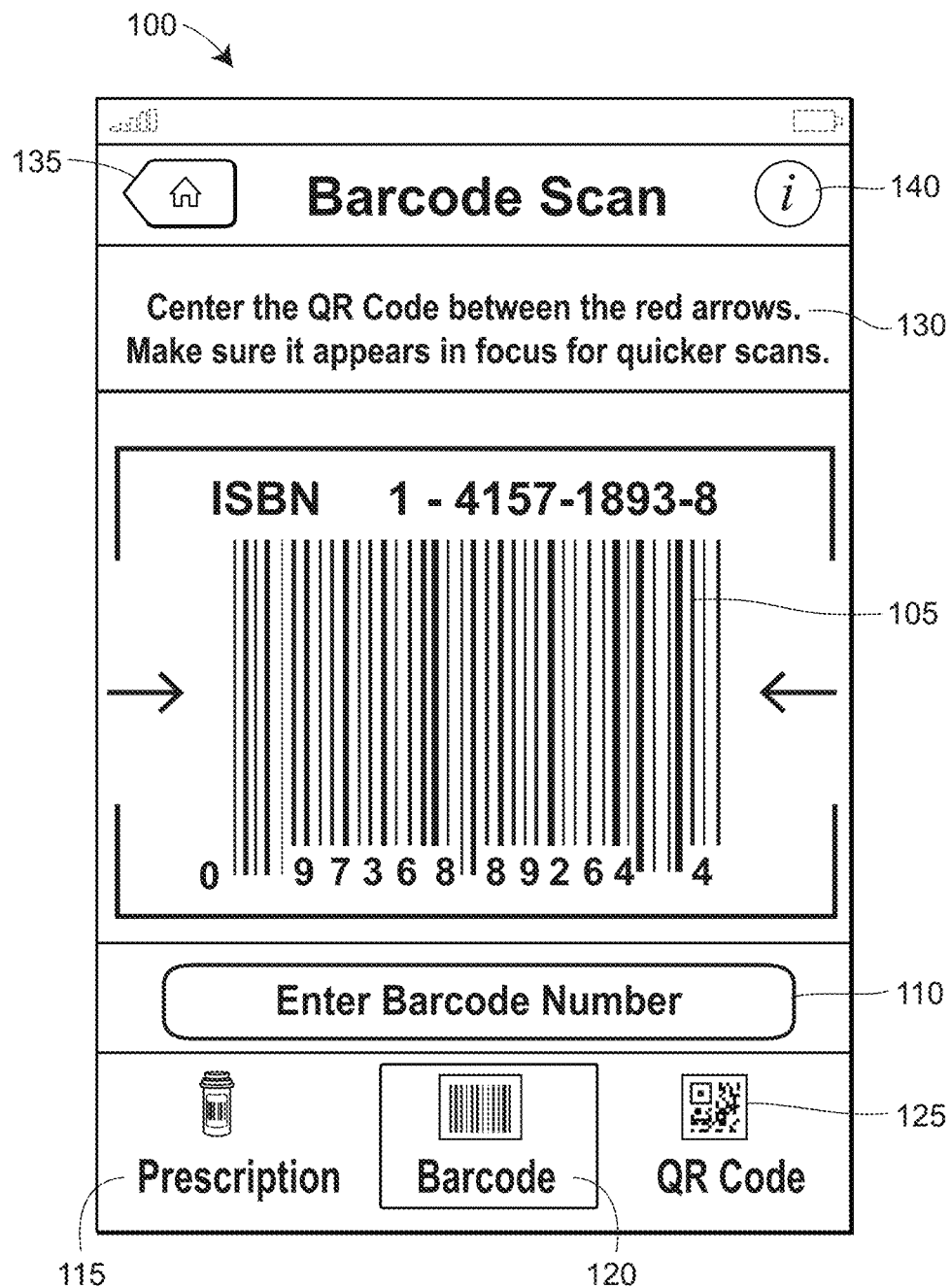
FIG. 1 depicts an example prescription label data entry user interface.

Turning to FIG. 1, a prescription status data user interface 100 may include a barcode image display area 105, a barcode number data entry area 110, a prescription information selection icon 115, a barcode scan selection icon 120, a quick code scan selection icon 125, a user instruction information banner area 130, a home screen selection icon 135, and a general prescription status data information selection icon 140. As described in detail herein, a user may implement the user interface 100 to obtain prescription label data by either scanning a barcode or by manually entering the prescription label data.

For example, an automatic prescription status data access system of the present disclosure may allow a user to scan a barcode of any type (e.g., Universal Product Code (UPC), Quick Response Code (QR Code), prescription barcode, etc.) via, for example, an internet-enabled device, and the system may determine a barcode type for the barcode, decodes the barcode using the barcode type, and automatically retrieve data associated with the decoded barcode according to the barcode type. To scan a barcode of any type, the user may launch a client application on an internet-enabled device, and may navigate to an image capture screen (e.g., user interface 100 of FIG. 1) within the client application. After receiving a command from the user to display the image capture screen, the client application may execute an image capture routine that may coordinate with an image capture device to provide image data (e.g., barcode display 105 of FIG. 1) to the client application. In response to receiving the command to display the image capture screen, the client application may additionally execute a barcode scanning routine that determines a barcode type of the barcode from image data, and may decode the barcode into, for example, decoded prescription label data according to the barcode type. Thereafter, a dynamic prescription status data access system may automatically retrieve prescription status data according to the barcode type and associated with the decoded prescription label data.

Figure 2A:
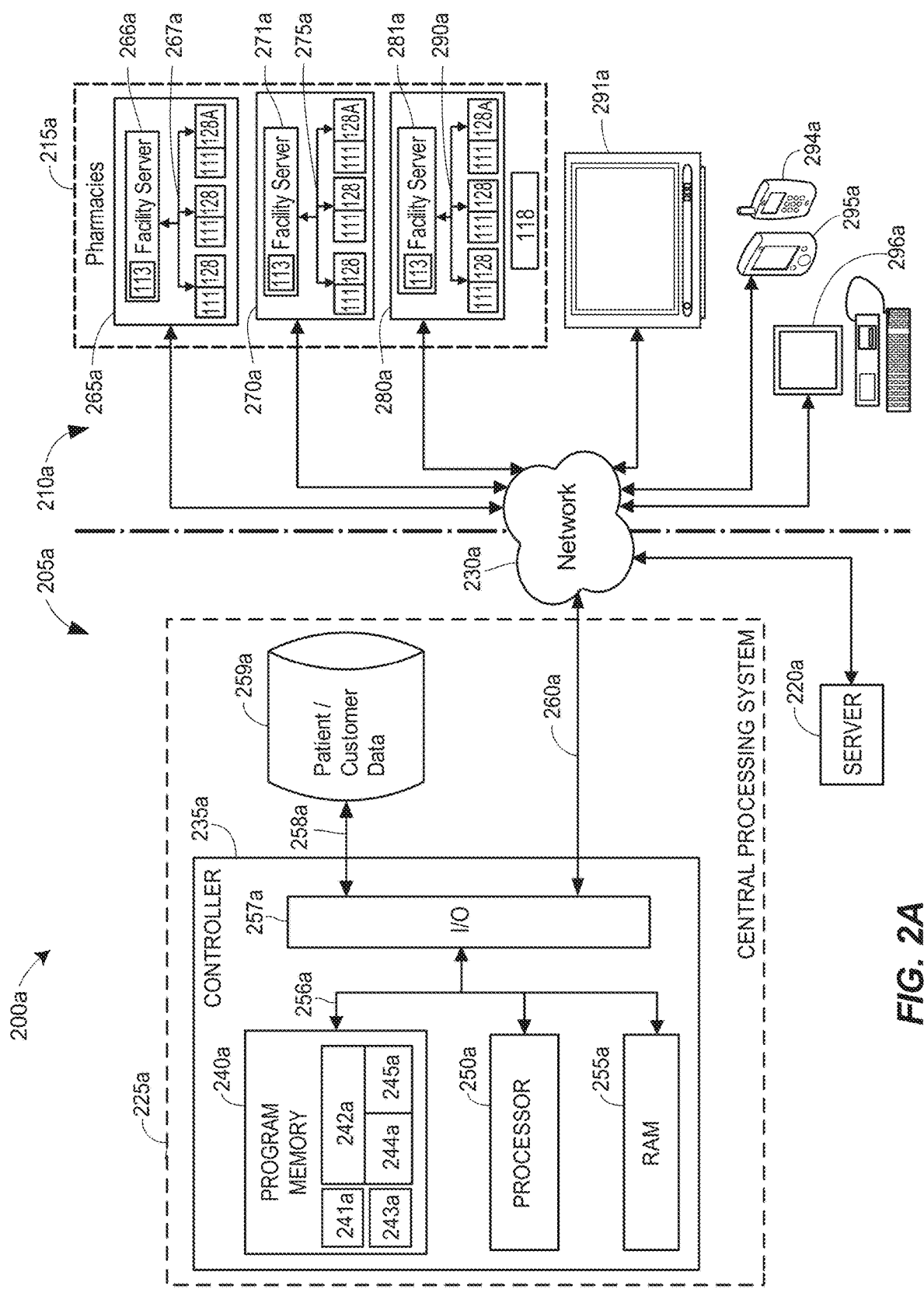
FIG. 2A depicts a block diagram of an example computer network and system on which an exemplary dynamic prescription status data access systems and methods may operate.

With reference to FIG. 2A, various aspects of an exemplary computer system architecture for implementing a dynamic prescription status data access system 200a may include front-end components 210a and back-end components 205a. The front-end components 210a are primarily disposed within a retail network 215a including one or more pharmacies 265a, 270a, 280a. The pharmacies 265a, 270a, 280 may be located, by way of example rather than limitation, in separate geographic locations from each other, including different areas of the same city, different cities, or even different states. The front-end components 210a comprise a number of pharmacy workstations 128. The pharmacy workstations 128 are local computers located in the various pharmacies 265a, 270a, 280 throughout the retail network 215a and executing various pharmacy management-related applications 111, 113, 128a. Pharmacists, technicians, and other pharmacy personnel, referred to collectively herein simply as "pharmacists" (not shown), use the pharmacy workstations 128 to access customer information, enter new prescriptions, access insurance and payment information and so fourth. Each of the pharmacies 265a, 270a, 280 may be, for example, an in-store retail pharmacy, an on-line pharmacy, a mail-order pharmacy, a long-term care pharmacy, a workplace/on-site pharmacy, or a specialty pharmacy. The retail network 215a may also include one or more warehouses or central-filling facilities 118. The warehouses or central-filling facilities 118 may distribute medications or retail products to the various retail pharmacies 265*a*, 270*a*, 280 in the retail network 215*a*, or may distribute medications or retail products directly to customers. Internet-enabled devices (e.g., personal computers 296*a*, cellular phones 294*a*, smart phones 295*a*, internet-enabled televisions 291*a*, etc.) may be communicatively connected to the pharmacies 265*a* and to a system 225*a* through a digital network 230*a*, as described below.

Those of ordinary skill in the art will recognize that the front-end components 245*a* could also comprise a plurality of facility servers 220*a* disposed at the plurality of pharmacies 265*a* instead of, or in addition to, a plurality of pharmacy workstations 128. Each of the pharmacies 265*a* may include one or more facility servers 220*a* that may facilitate communications between the workstations 128 of the pharmacies 265*a* via a digital network 230*a*, and may store information for a plurality of customers/employees/accounts/etc. associated with each facility. Of course, a local digital network 267*a*, 275*a*, 290*a* may also operatively connect each of the workstations 128 to the facility server 220*a*. Unless otherwise indicated, any discussion of the workstations 128 also refers to the facility servers 220*a*, and vice versa. Moreover, environments other than the pharmacies 265*a* may employ the workstations 128 and the servers 220*a*. As used herein, the term "pharmacy" refers to any of these environments (e.g., call centers, kiosks, Internet interface terminals, etc.) in addition to the retail pharmacies 265*a*, etc. described above.

The front-end components 245*ba* communicate with the back-end components 205*a* via the digital network 230*a*. One or more of the front-end components 245*ba* may be excluded from communication with the back-end components 205*a* by configuration or by limiting access due to security concerns. For example, the internet-enabled devices 291*a*-296*a* may be excluded from direct access to the back-end components 205*a*. In some embodiments, the pharmacies 265*a* may communicate with the back-end components via the digital network 230*a*. In other embodiments, the pharmacies 265*a* and internet-enabled devices 291*a*-296*a* may communicate with the back-end components 205*a* via the same digital network 230*a*, but digital access rights, IP masking, and other network configurations may deny access to the internet-enabled devices 291*a*-296*a*.

The digital network 230*a* may be a proprietary network, a secure public Internet, a virtual private network or some other type of network, such as dedicated access lines, plain ordinary telephone lines, satellite links, combinations of these, etc. Where the digital network 230*a* comprises the Internet, data communication may take place over the digital network 230*a* via an Internet communication protocol. In addition to one or more servers 220*a* (described below), the back-end components 205*a* include the central processing system 225*a* within a central processing facility, such as, for example, the central processing facility described in U.S. patent application Ser. No. 12/271,686 entitled "DISTRIBUTED PHARMACY PRESCRIPTION PROCESSING SYSTEM" the entire disclosure of which is incorporated by reference herein. Of course, the pharmacies 265*a* may be communicatively connected to different back-end components 205*a* having one or more functions or capabilities that are similar to the central processing system 225*a*. The central processing system 225*a* may include one or more computer processors 250*a* adapted and configured to execute various software applications and components of the automatic data access system 200*a*, in addition to other software applications. The central processing system 225*a* further includes a database 259*a*. The database 259*a* is adapted to store data related to the operation of the automatic data access system 200*a* (e.g., patient profile data including diagnoses, past healthcare product and medication purchases, prescription histories, etc.) The central processing system 225*a* may access data stored in the database 259*a* when executing various functions and tasks associated with the operation of the automatic data access system 200*a*.

Although FIG. 2A depicts the automatic data access system 200*a* as including the central processing system 225*a* in communication with three pharmacies 265*a*, and various internet-enabled devices 291*a*-296*a* it should be understood that different numbers of processing systems, pharmacies, and devices may be utilized. For example, the digital network 230*a* (or other digital networks, not shown) may interconnect the central processing system 225*a* to a plurality of included central processing systems 225*a*, hundreds of pharmacies 265*a*, and thousands of internet-enabled devices 291*a*-296*a*. According to the disclosed example, this configuration may provide several advantages, such as, for example, enabling near real-time uploads and downloads of information as well as periodic uploads and downloads of information. This provides for a primary backup of all the information generated in the automatic data access process. Alternatively, some of the pharmacies 265*a* may store data locally on the facility server 207*ba* and/or the workstations 128.

FIG. 2A also depicts one possible embodiment of the central processing system 225*a*. The central processing system 225*a* may have a controller 235*a* operatively connected to the database 259*a* via a link 258*a* connected to an input/output (I/O) circuit 257*a*. It should be noted that, while not shown, additional databases may be linked to the controller 235*a* in a known manner.

The controller 235*a* may include a program memory 240*a*, the processor 250*a* (may be called a microcontroller or a microprocessor), a random-access memory (RAM) 255*a*, and the input/output (I/O) circuit 257*a*, all of which are interconnected via an address/data bus 256*a*. It should be appreciated that although only one microprocessor 250*a* is shown, the controller 235*a* may include multiple microprocessors 250*a*. Similarly, the memory of the controller 235*a* may include multiple RAMs 255*a* and multiple program memories 240*a*. Although the I/O circuit 257*a* is shown as a single block, it should be appreciated that the I/O circuit 257*a* may include a number of different types of I/O circuits. The RAM(s) 255*a* and the program memories 240*a* may be implemented as semiconductor memories, magnetically readable memories, and/or optically readable memories, for example. A link 260*a* may operatively connect the controller 235*a* to the digital network 230*a* through the I/O circuit 257*a*.

The program memory 240*aa* may also contain machine-readable instructions (i.e., software) 242*a*, for execution by the processor 250*a*. The software 242*a* may perform the various tasks associated with operation of the pharmacy or pharmacies, and may be a single module 242*a* or a plurality of modules 241*a*-245*a*. While the software 242*a* is depicted in FIG. 2A as including five modules, 241*a*-245*a*, the software 242*a* may include any number of modules accomplishing tasks related to pharmacy operation including, for example, receiving prescription orders, managing prescription workflow, etc. The central processing system 225*a* implements a server application 242*a* for providing data to a user interface application 241*a* operating on the workstations 128.

For purposes of implementing the automatic data access system 200*a*, the user interacts with the server 220*a* and the pharmacy systems (e.g., the central processing system 225a) via an internet-enabled device 291a-296a (e.g., mobile device application, etc.), a specialized application, or a plurality of web pages.

Figure 2B:
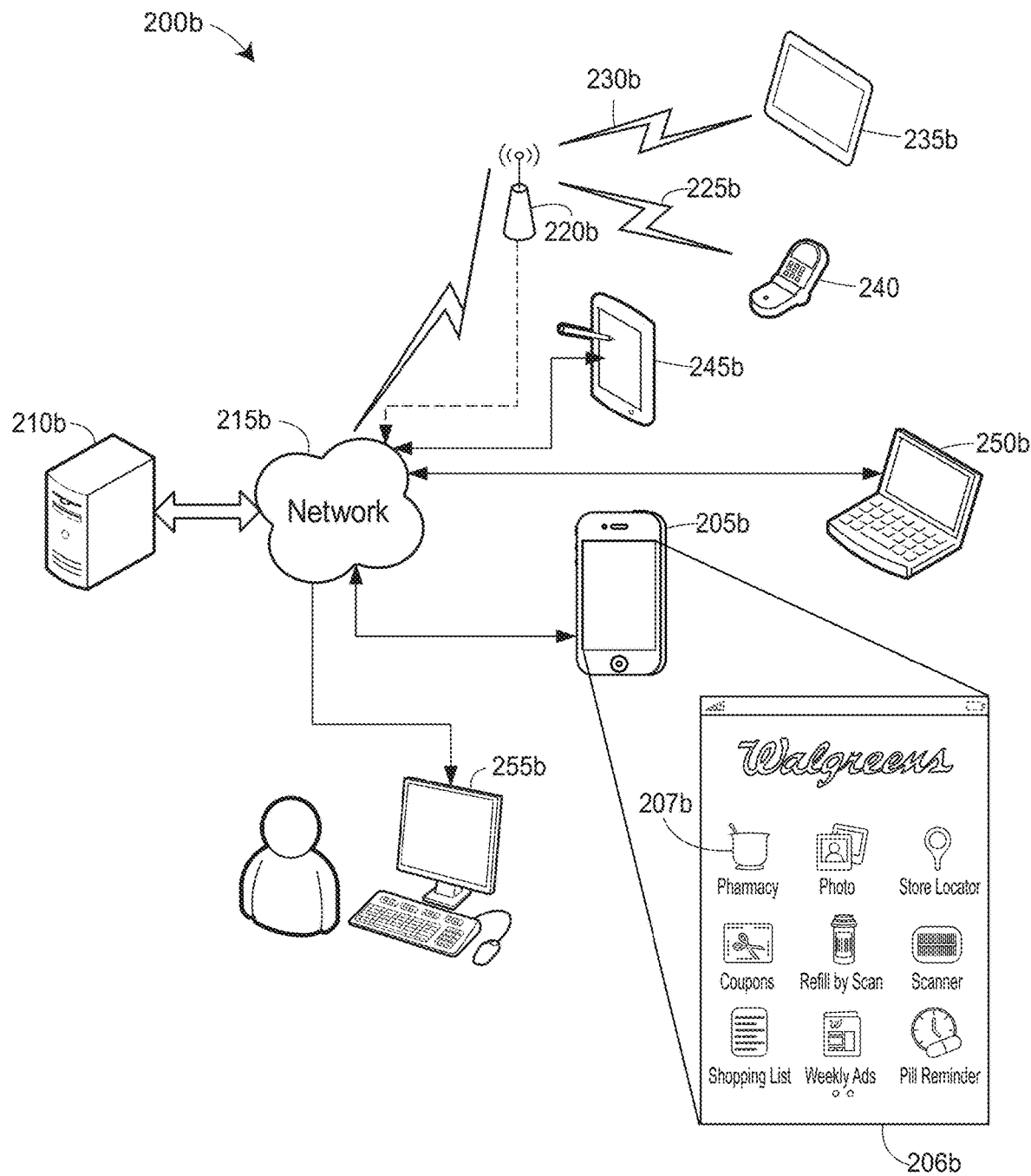
FIG. 2B depicts example internet-enabled devices and associated equipment that may operate with a network and a server to implement dynamic prescription status data access systems and methods may operate.

Turning to FIG. 2B, a server 210b may be connected, via the network 215b, to internet-enabled devices 291a-296a through which a user may initiate and interact with the automatic data access system 200a (as shown in FIG. 2A). The internet-enabled devices 291a-296a may include, by way of example, a tablet computer 235b, an internet-enabled cell phone 205b, a personal digital assistant (PDA) 245b, a mobile device smart-phone 205b also referred to herein as a "mobile device," a laptop computer 250b, a desktop computer 255, a portable media player (not shown), etc. Of course, any internet-enabled device appropriately configured may interact with the automatic data access system 200a. The internet-enabled devices 291a-296a need not necessarily communicate with the network 215b via a wired connection. In some instances, the internet-enabled devices 291a-296a may communicate with the network 215b via wireless signals 225b and, in some instances, may communicate with the network 215b via an intervening wireless or wired device 220b, which may be a wireless router, a wireless repeater, a base transceiver station of a mobile telephony provider, etc. Each of the internet-enabled devices 291a-296a may interact with the server 210b to receive web pages or server data from the server 220a and may display the web pages or server data via a client application (described below). For example, the mobile device 205b may display a home screen 206b (i.e., the root or start page at which users enter the client application) of the client application to user, may receive an input from the user, and may interact with the server 210b depending on the type of user-specified input. It will be appreciated that although only one server 210b is depicted in FIG. 2B, multiple servers 210b may be provided for the purpose of distributing server load, serving different web pages, implementing different portions of the pharmacy web interface, etc. These multiple servers 220a may include a web server, an entity-specific server (e.g. an Apple® server, etc.), a server that is disposed in a retail or proprietary network, an independent third-party server that is not under the control of the entity, etc.

As described above, the database 259a, illustrated in FIG. 2A, may include various information about the pharmacy's customers and the prescriptions filled by the pharmacy, as well as basic biographical information about the customer, such as a customer name, a customer address, a customer phone number, and the like. Customer records are among the exemplary data that the automatic data access system 200a may store on the database 259a. The customer record also includes prescription data for each prescription filled by the pharmacy for the customer. The prescription data generally include, but are not limited to: a name of the medication; an indication whether a generic may be substituted; a dose (i.e., pills per day) of the medication; a number of days of medication to be dispensed (also referred to herein as a "day supply" or a "prescribed day supply"); a number of refills prescribed; a number of refills remaining; a prescription date; a prescribing physician; a phone number for the prescribing physician; a date on which the prescription was most recently adjudicated; a calculated date on which the prescription may next be adjudicated for the prescription; a remaining day supply for the prescription; a percent-consumption period indicating the number of days it would take to consume the required minimum percent-fill consumed of the fill for the prescription); and a prescription number. Of course, the prescription data need not include all of the information above, such as when the automatic data access system 200a determines some information (e.g., the next adjudication date) but does not store it, or stores it some place other than with the prescription data in the database 259a. Moreover, the prescription data may include additional information not mentioned above.

As shown in FIG. 2B, to access the server 220a, the facility servers 210b, or the server applications 242a, the user executes the client application 207b on one of the internet-enabled devices 291a-296a, such as the mobile device 205b. Using the client application 207b, the user may request server data (not shown) by navigating a series of client application screens, such as the home screen 206b of the client application 207b. FIGS. 1, 4, 5B-5F, 6A, 6B, 6D, 6E, 7A and 7C-8D depict client application user interfaces or screens that the server 220a, the facility servers 210b, or the server applications 241a-245a may transmit in various embodiments of the automatic data access system 200a. In any event, the user may launch the client application 207b from one of the internet-enabled devices 291a-296a via any suitable manner, such as touch-selecting a client application icon 207b on the display 206b of the mobile device 205b, double-clicking on the client application icon via a mouse of a computer 255b or a trackpad (not shown) of a laptop 250b. After the user launches the client application 207b, the home screen 206b of the client application 207b is displayed to the user on the mobile device 205b.

Figure 3:
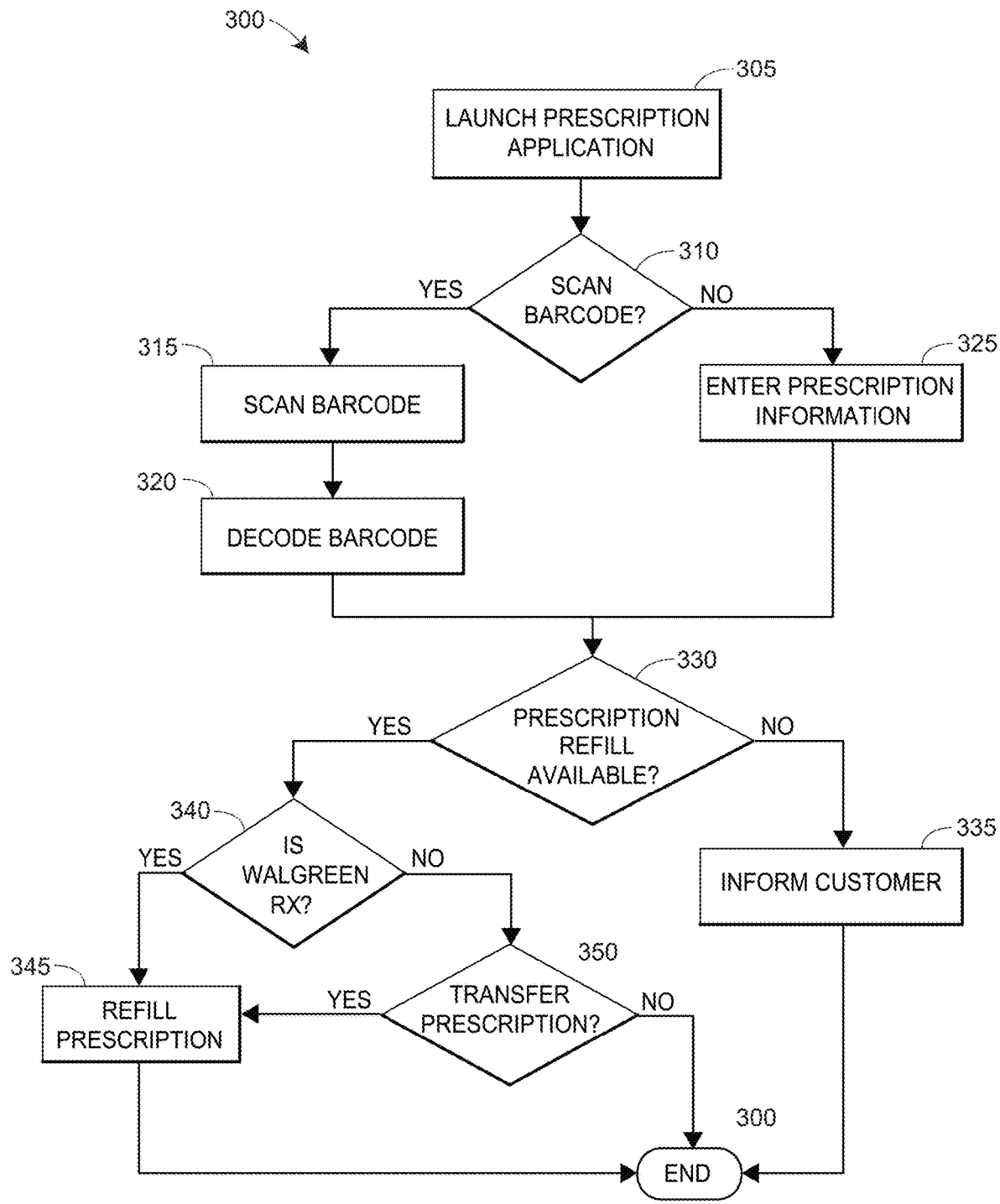
FIG. 3 depicts a flow diagram for an example method for automatic prescription status data access.

With reference to FIG. 3, a method for dynamically accessing prescription status data 300 may include a processor (e.g., processor 250a of FIG. 2A) launching a prescription application (block 305). The processor 250a may generate an inquiry as to whether a user wishes to scan a barcode (block 310). If the processor 250a determines that the user does not wish to scan a barcode (block 310), the processor 250a may generate a user interface (e.g., user interface 100 of FIG. 1 or user interface 400 of FIG. 4) to allow the user to manually enter a prescription label number (block 325). If the processor 250a determines that the user wishes to can a barcode (block 310), the processor 250a may cause an associated barcode scanner to scan a bar code (block 315). The processor 250a may decode the scanned barcode to, for example, generate prescription label data (block 320).

The processor 250a may determine whether a prescription refill is available based, for example, on the prescription label data (block 330). When the processor 250a determines that no prescription refill is available (block 330), the processor 250a may automatically generate a prescription status message to, for example, inform the user that an associated prescription has already been filled (block 335). When the processor 250a determines that a prescription refill is available (block 330), the processor 250a may determine whether the available prescription refill is associated with a first pharmacy (e.g., Walgreen) (block 340). When the processor 250a determines that the available prescription refill is associated with the first pharmacy (block 340), the prescription may be automatically refilled (block 345). When the processor 250a determines that the available prescription refill is not associated with the first pharmacy (block 340), the processor 250a may automatically initiate a prescription transfer request to determine whether the user wishes to transfer the available prescription refill from, for example, a second pharmacy to the first pharmacy (block 350). When the processor 250a determines that the user wishes to transfer the prescription to the first pharmacy (block 350), the processor 250a may automatically fill the prescription (block 345). Once the processor 250a either fills the prescription (block 345) or determines that the user does not want to transfer the prescription (block 350), the processor 250a may end the method of dynamically accessing prescription status data (block 355).

Figure 4:
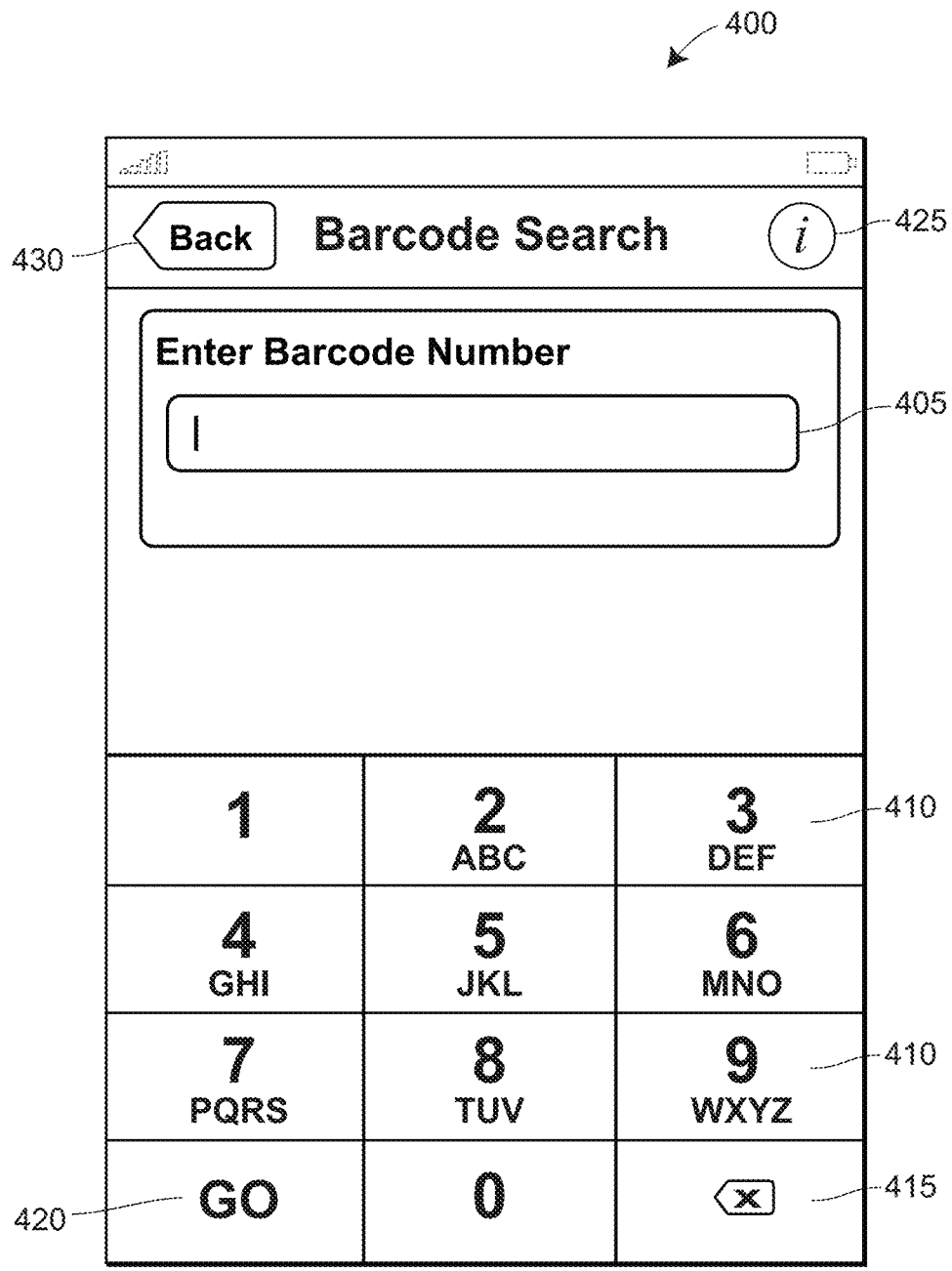
FIG. 4 depicts an example prescription label data entry user interface.

Turning to FIG. 4, a prescription status data user interface 400 may include a prescription label number (e.g., barcode number) entry area 405, a keyboard 410, a return selection icon 415, an enter selection icon 420, a back selection icon 430, and a prescription status data information selection icon 425. A user may implement the user interface 400 to, for example, manually enter a prescription label number into the prescription label number entry area 405 using the keyboard 410.

Figure 5A:
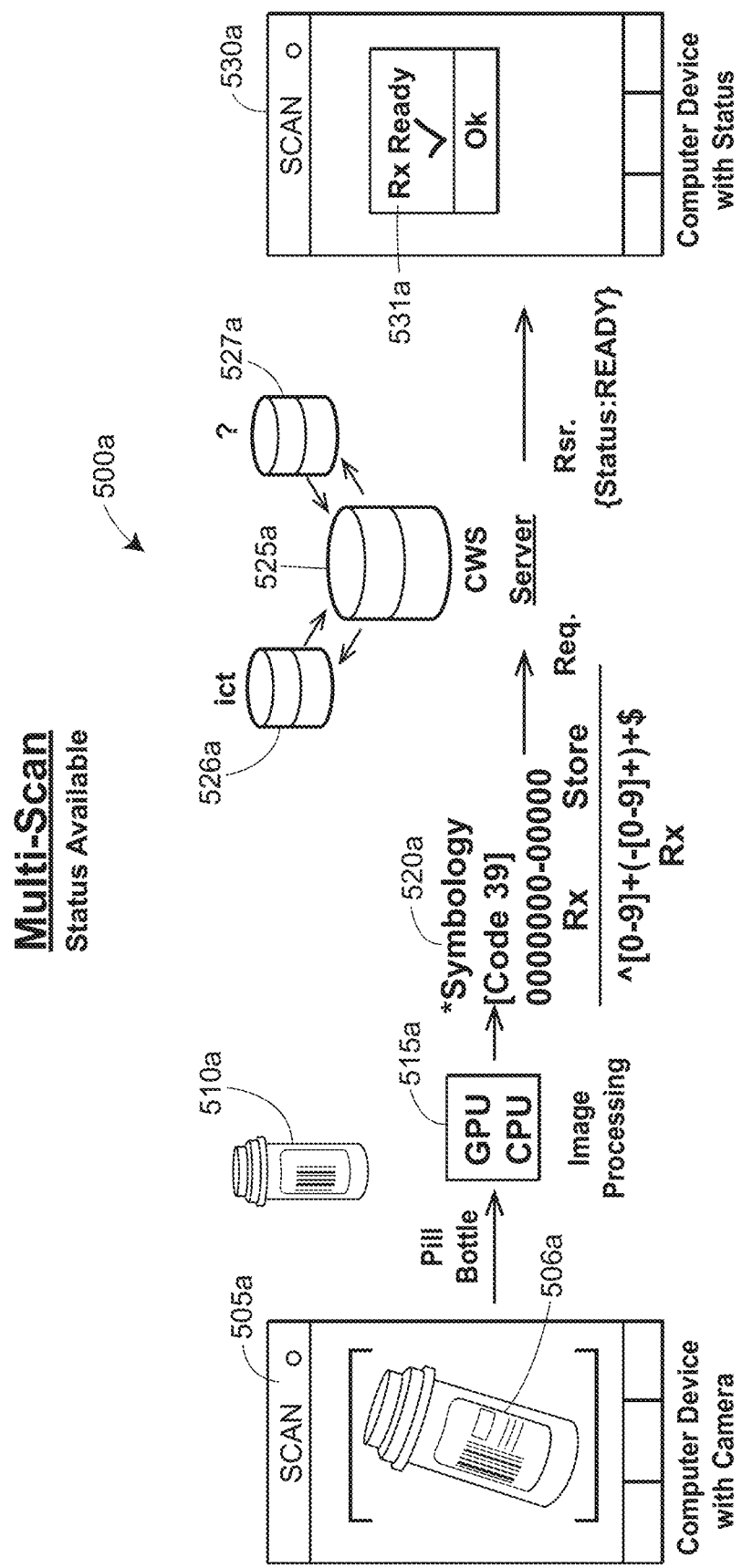
FIGS. 5A-5F depict an example system and associated devices with user interfaces for dynamic prescription status data access.

With reference to FIGS. 5A-5F, an example system 500a and associated devices with user interfaces 500b-f are depicted for dynamic prescription status data access. As depicted in FIG. 5A, the system may include a user device 505a having a user interface 506a for scanning a barcode 506a representative of a prescription label number, or manually entering a prescription label number. For example, a barcode on a pill bottle 510a may be scanned and a graphical processing unit 515a may decode the barcode to generate prescription label data that is representative of a prescription label number. Symbology 520a may be associated with a prescription label number. Prescription status data may be automatically retrieved from any one of the databases 525a, 526a, 527a based on prescription label data. The user device 530a may automatically generate a prescription status message 531a based on, for example, the prescription status data.

Figure 5B:
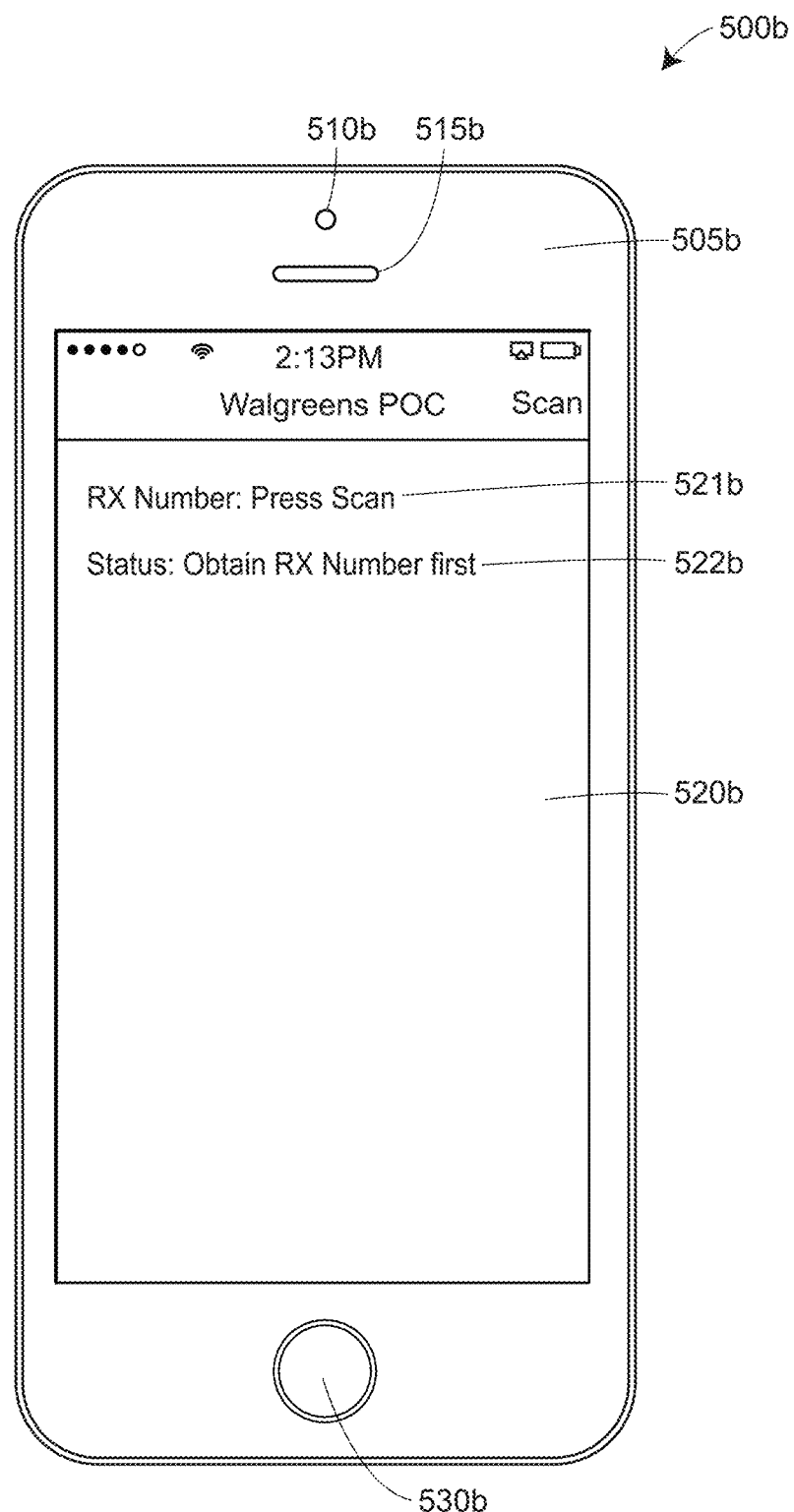

As illustrated in FIG. 5B, a dynamic prescription status information access system 500b may include a user device 505b having a camera 510b, a speaker 515b, a user interface display 520b, and a microphone 530b. Accordingly, the user device 505b may include voice recognition features for audible input of a barcode number, or other prescription information. The user interface display 520b may include a barcode scan instruction (e.g., press scan) 521b and a prescription status message (e.g., Obtain Rx Number first) 522b. The user device 505b may be similar to, for example, any one of the internet-enabled devices 291a-296a of FIG. 2A. A user of the device 505b may, for example, select a scan feature and take an image of a barcode using the camera 510b via a user interface (e.g., user interface 100 of FIG. 1). Alternatively, a user of the device 505b may, for example, manually enter a prescription label number via a user interface (e.g., user interface 400 of FIG. 4).

Figure 5C:
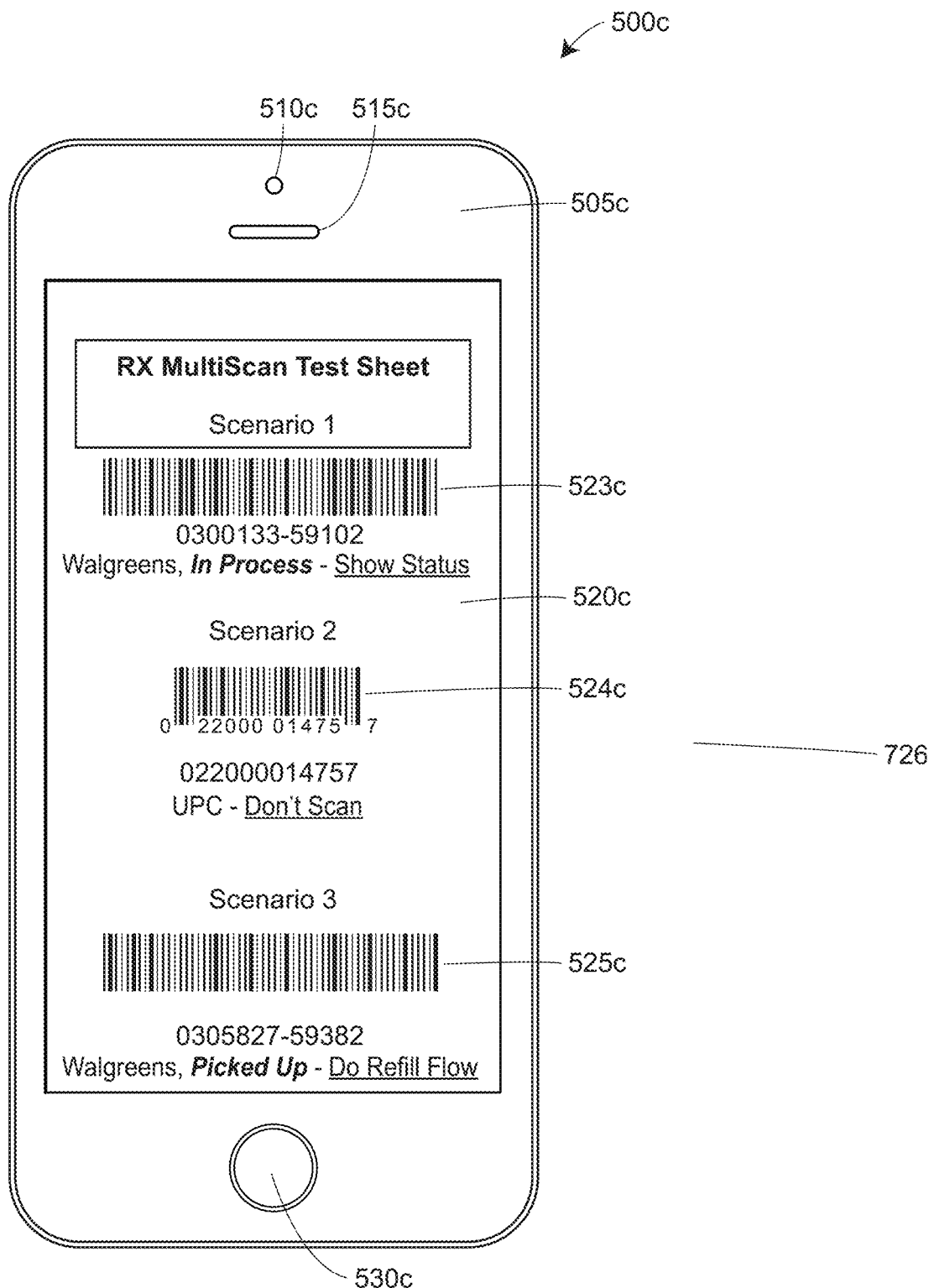

As illustrated in FIG. 5C, a dynamic prescription status information access system 500c may include a user device 505c having a camera 510c, a speaker 515c, a user interface display 520c, and a microphone 530c. The user interface display 520c may include a first barcode scan scenario (e.g., show status) 523c, a second barcode scan scenario (e.g., don't scan) 524c, and a third barcode scan scenario (e.g., do refill flow) 525c. The user device 505c may be similar to, for example, any one of the internet-enabled devices 291a-296a of FIG. 2A.

Figure 5D:
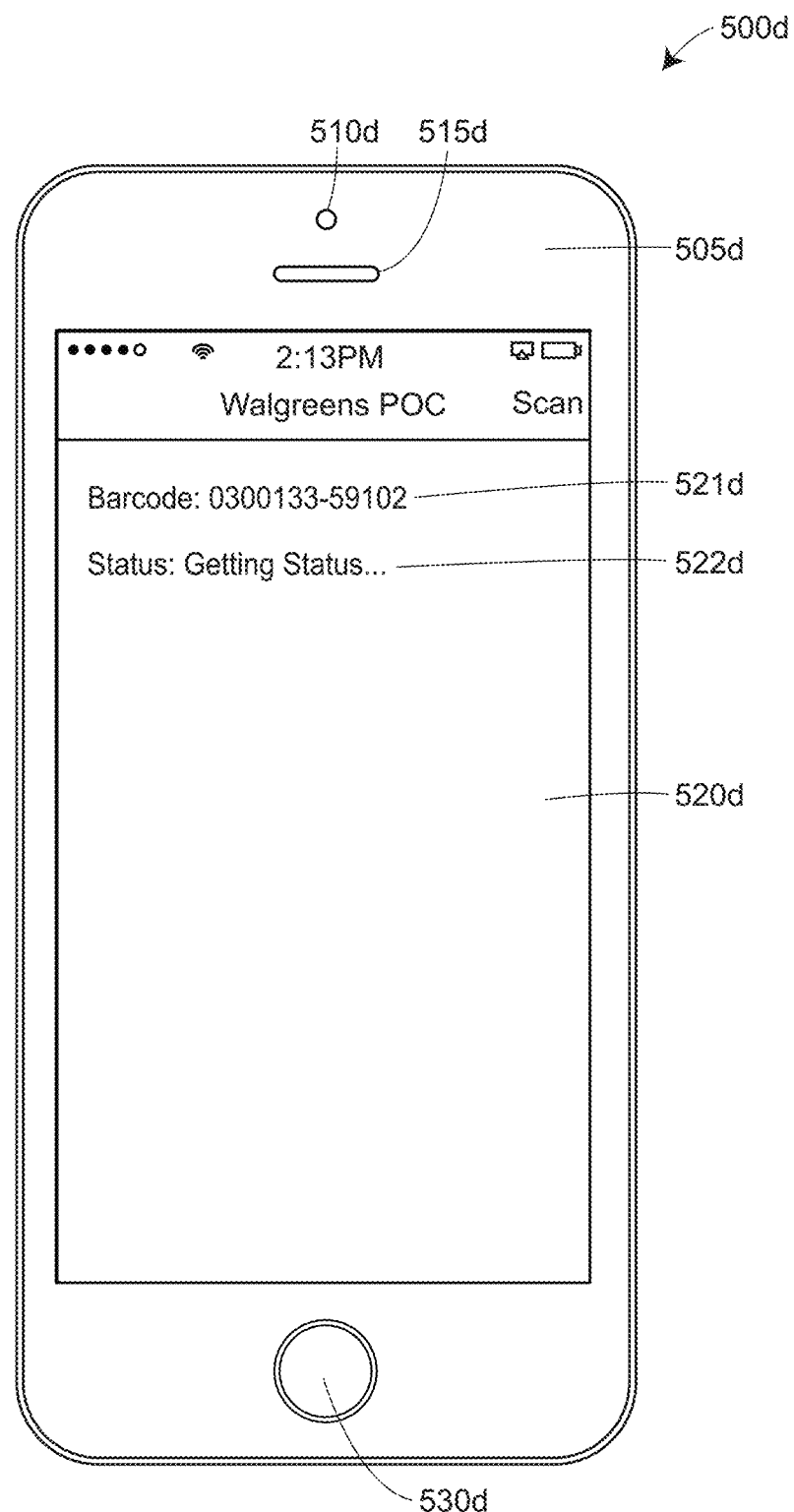

As illustrated in FIG. 5D, a dynamic prescription status information access system 500d may include a user device 505d having a camera 510d, a speaker 515d, a user interface display 520d, and a microphone 530d. The user interface display 520d may include a barcode scan instruction (e.g., a prescription label number) 521d and a prescription status message (e.g., getting status . . . ) 522d. The user device 505d may be similar to, for example, any one of the internet-enabled devices 291a-296a of FIG. 2A.

Figure 5E:
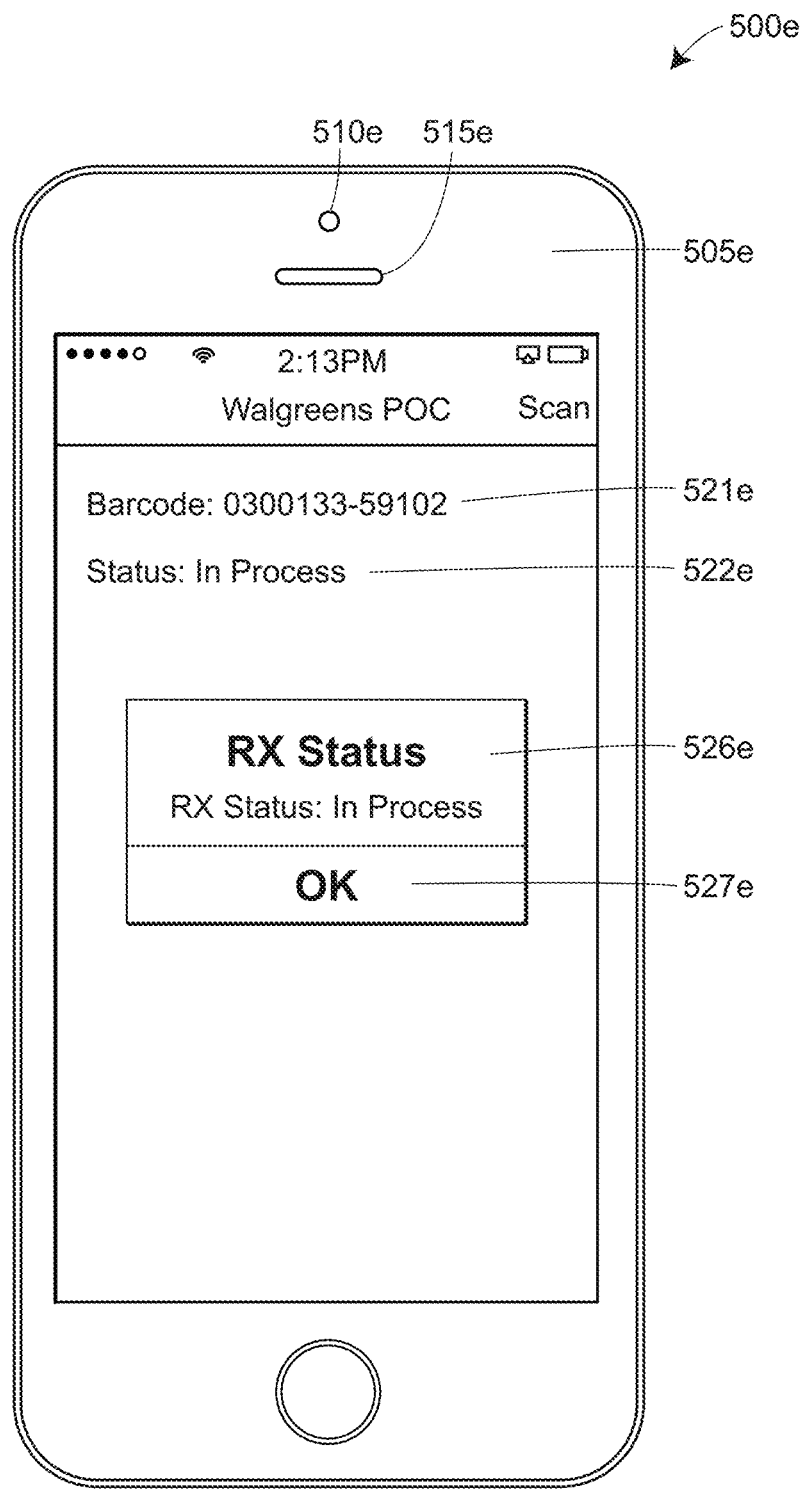

As illustrated in FIG. 5E, a dynamic prescription status information access system 500e may include a user device 505e having a camera 510e, a speaker 515e, a user interface display 520e, and a microphone 530e. The user interface display 520e may include a barcode scan instruction (e.g., a prescription label number) 521e, a prescription status message (e.g., in process) 522e, and a Rx status banner 526e with an OK selection icon 527e. The user device 505e may be similar to, for example, any one of the internet-enabled devices 291a-296a of FIG. 2A.

Figure 5F:
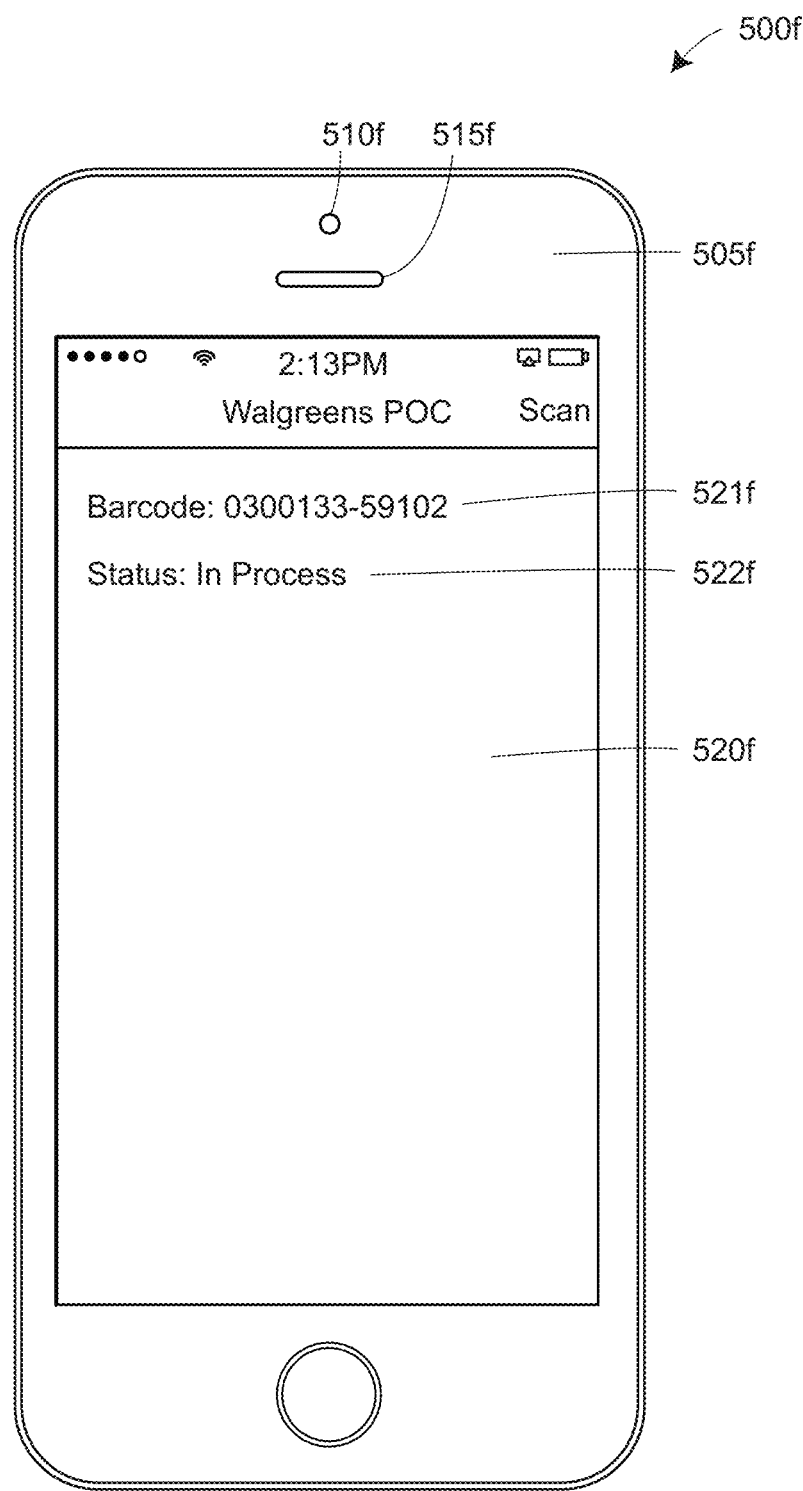

As illustrated in FIG. 5F, a dynamic prescription status information access system 500f may include a user device 505f having a camera 510f, a speaker 515f, a user interface display 520f, and a microphone 530f. The user interface display 520f may include a barcode scan instruction (e.g., a prescription label number) 521f and a prescription status message (e.g., in process) 522f. The user device 505f may be similar to, for example, any one of the internet-enabled devices 291a-296a of FIG. 2A.

Figure 6A:
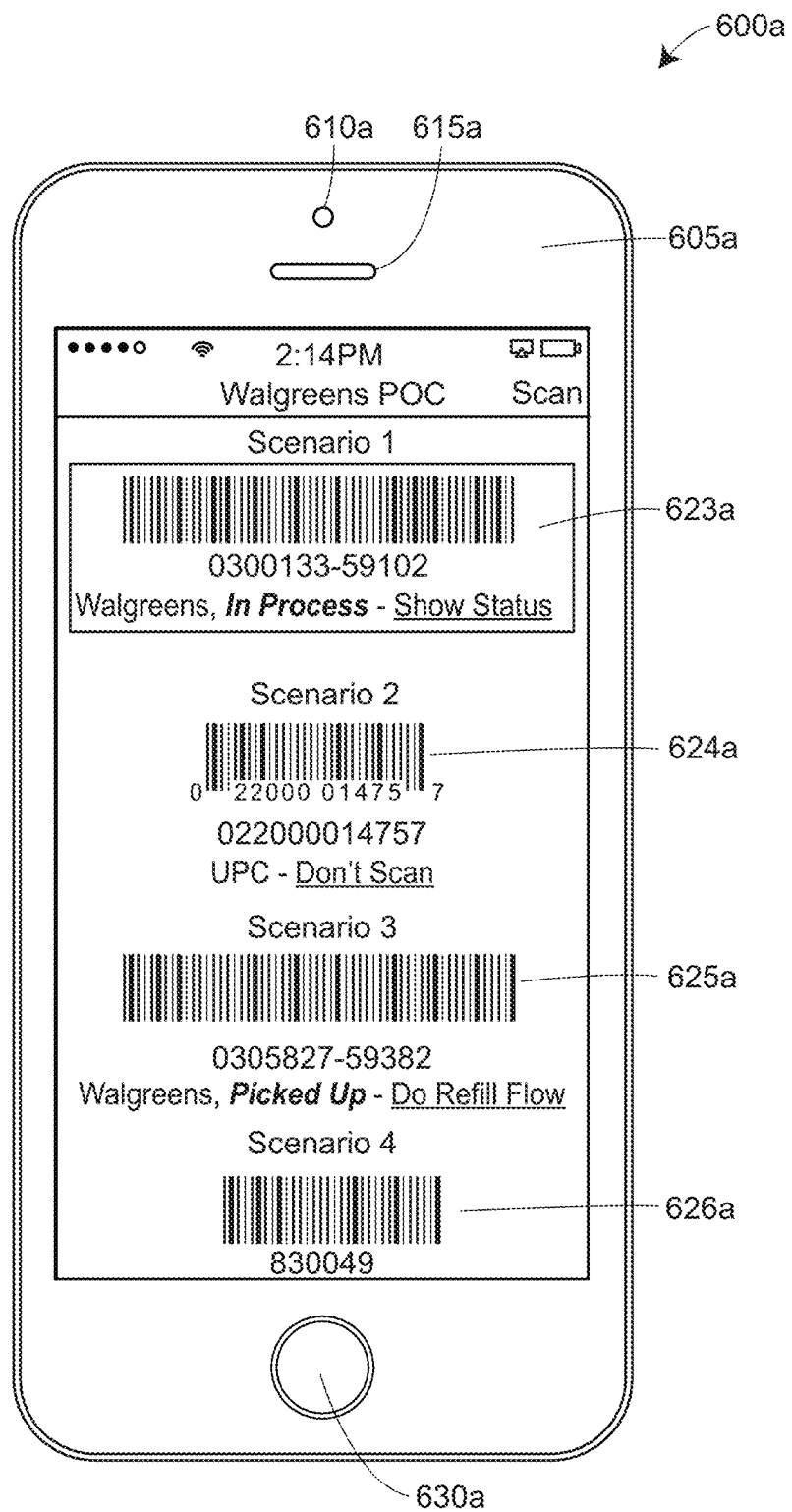
FIGS. 6A-6E depict an example system and associated devices with user interfaces for dynamic prescription status data access in response to manually entering a prescription label number.

Turning to FIGS. 6A-6E, an example system 600c and associated devices with user interfaces 600a, 600b, 600d, 600e are depicted for dynamic prescription status data access in response to manually entering a prescription label number. As illustrated in FIG. 6A, a dynamic prescription status information access system 600a may include a user device 605a having a camera 610a, a speaker 615a, a user interface display 620a, and a microphone 630a. The user interface display 620a may include a first barcode scan scenario (e.g., show status) 623a, a second barcode scan scenario (e.g., don't scan) 624a, a third barcode scan scenario (e.g., do refill flow) 625a, and a fourth barcode scan scenario 626a. The user device 605a may be similar to, for example, any one of the internet-enabled devices 291a-296a of FIG. 2A. As indicated in FIG. 6A with the outline rectangle, the first barcode scan scenario (e.g., show status) 623a has been selected.

Figure 6B:
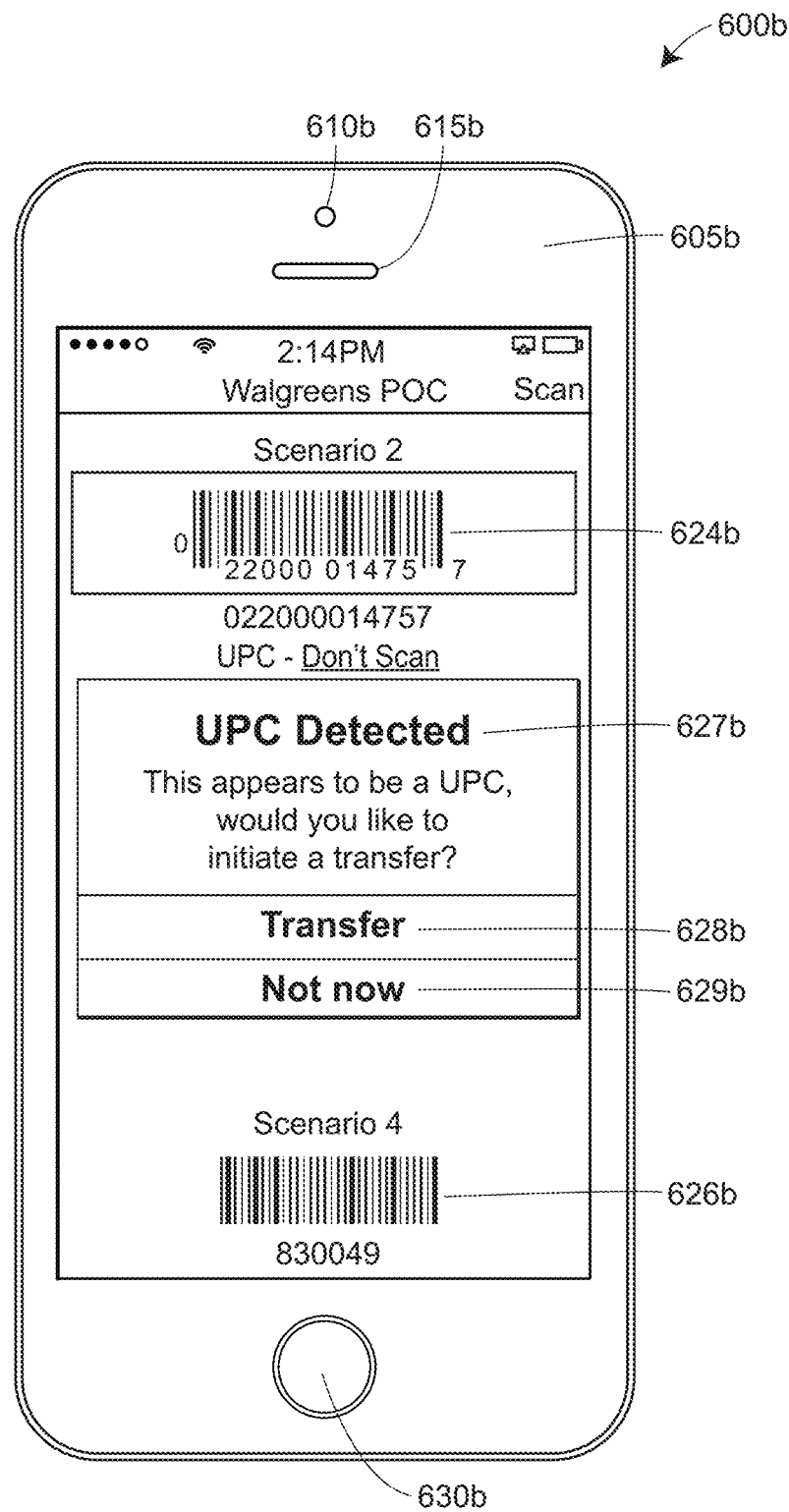

As illustrated in FIG. 6B, a dynamic prescription status information access system 600b may include a user device 605b having a camera 610b, a speaker 615b, a user interface display 620b, and a microphone 630b. The user interface display 620b may include a second barcode scan scenario (e.g., don't scan) 624b, a fourth barcode scan scenario 626b, and a UPC detected banner 627b having a prescription transfer selection icon 628b and a not now selection icon 629b. The user device 605 b may be similar to, for example, any one of the internet-enabled devices 291a-296a of FIG. 2A.

Figure 6C:
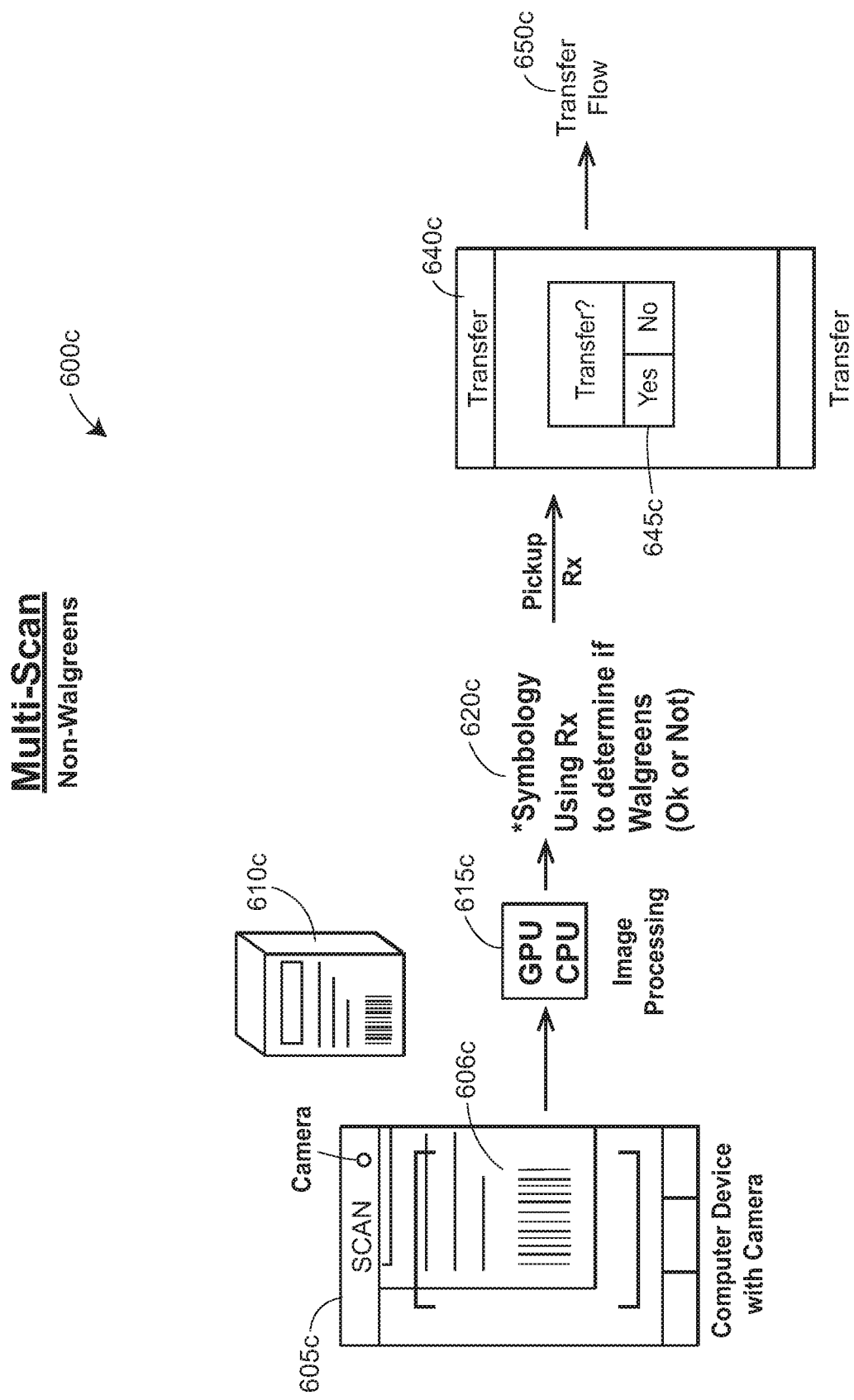

As illustrated in FIG. 6C, a dynamic prescription status information access system 600c may include a user device 605c having a user interface display 606c. The system 600c may further include a prescription pending with a second pharmacy 610c. The system may further include a graphical processing unit 615c for processing a scanned image of a barcode and symbology 620c encrypted within an associated barcode. As described in more detail with regard to FIGS. 8A-8D, the system 600c may include a prescription transfer user interface 640c having a prescription transfer selection icon 645c that, when selected by a user, may cause the device 605c to initiate a prescription transfer flow 650c.

Figure 6D:
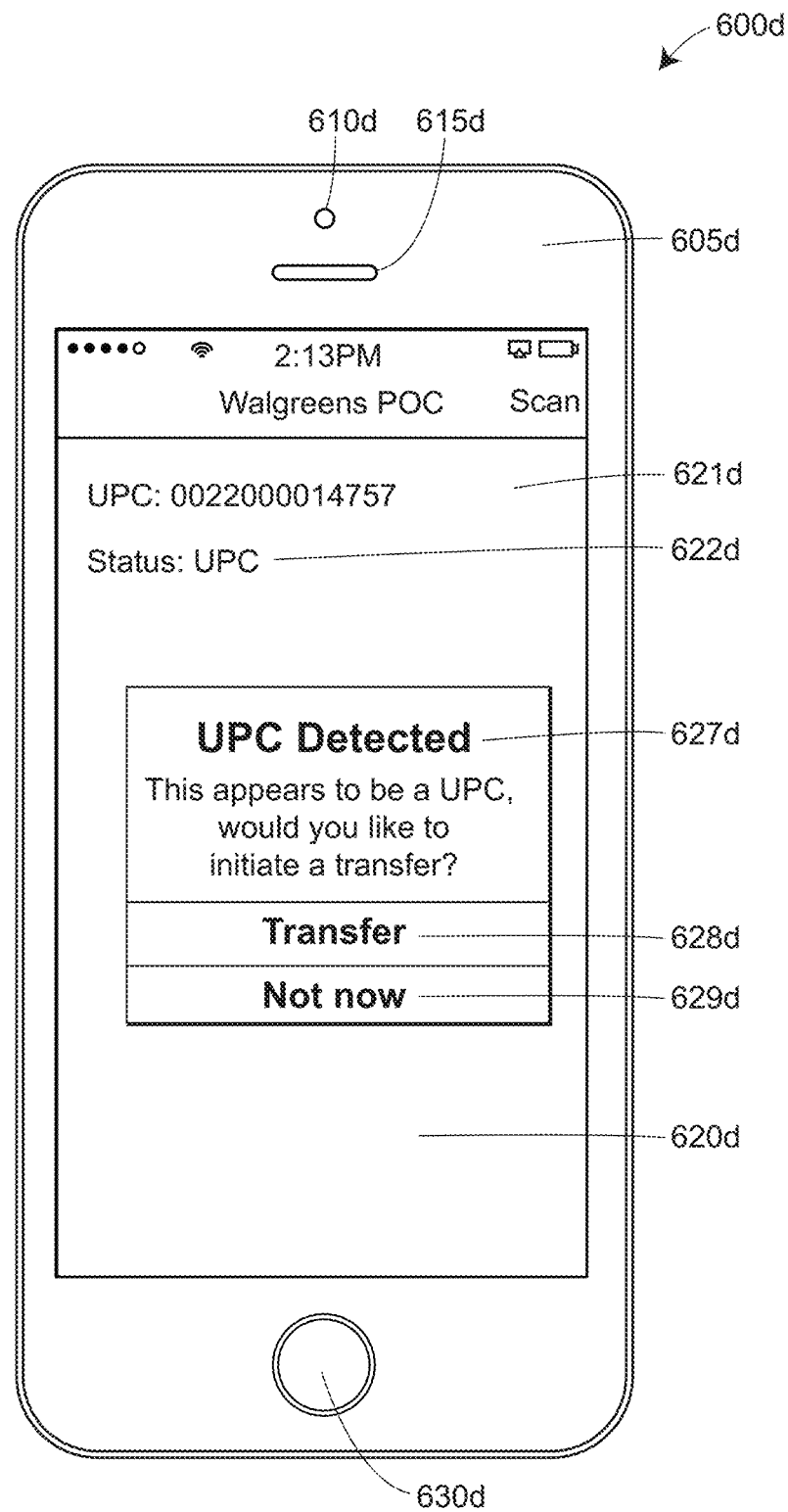

As illustrated in FIG. 6D, a dynamic prescription status information access system 600d may include a user device 605d having a camera 610d, a speaker 615d, a user interface display 620d, and a microphone 630d. The user interface display 620d may include a barcode scan instruction (e.g., a prescription label number) 621d, a prescription status message (e.g., UPC) 622d, and a UPC detection banner 627d having a prescription transfer selection icon 628d and a not now selection icon 629d. The user device 605d may be similar to, for example, any one of the internet-enabled devices 291a-296a of FIG. 2A.

Figure 6E:
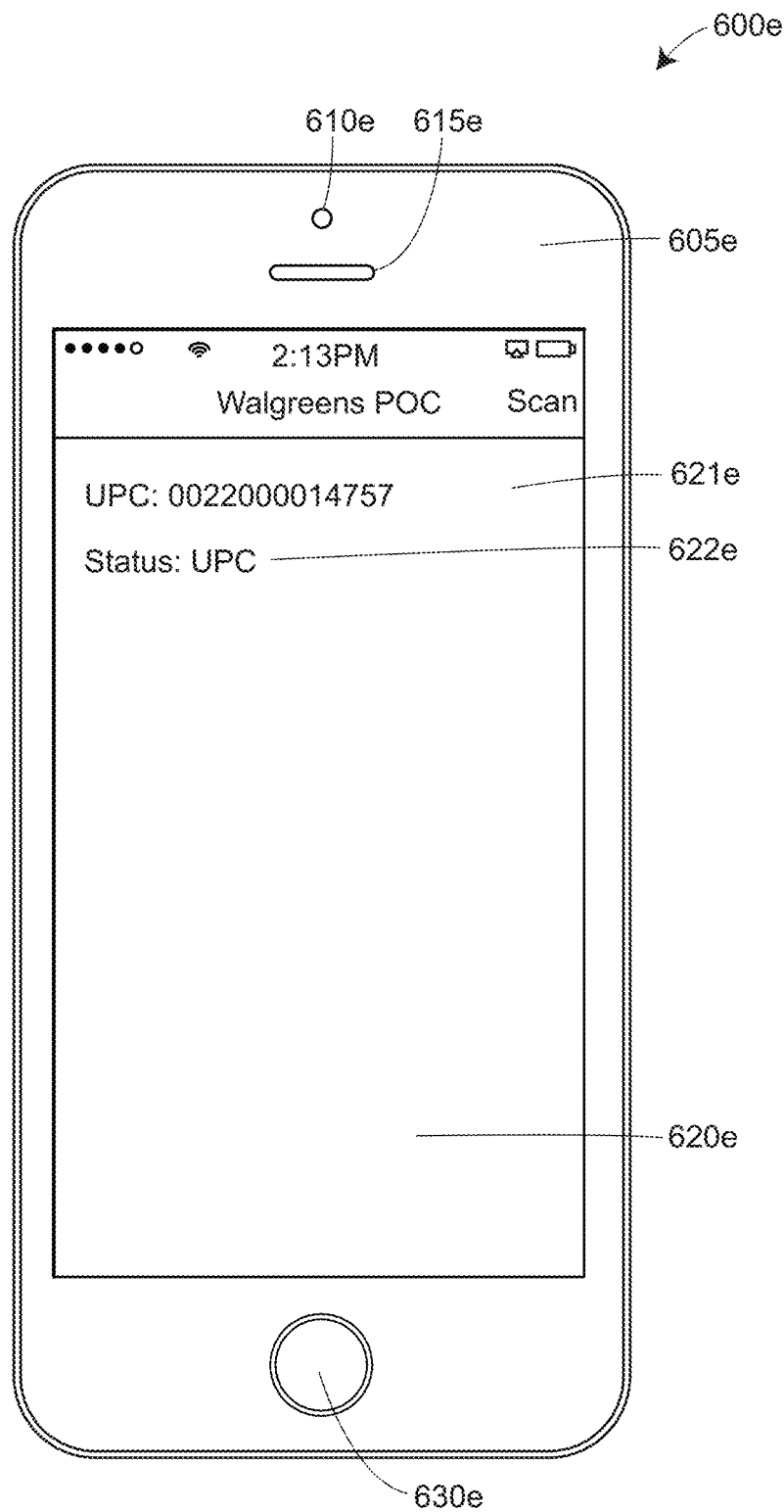

As illustrated in FIG. 6E, a dynamic prescription status information access system 600e may include a user device 605e having a camera 610e, a speaker 615e, a user interface display 620e, and a microphone 630e. The user interface display 620e may include a barcode scan instruction (e.g., a prescription label number) 621e and a prescription status message (e.g., UPC) 622e. The user device 605e may be similar to, for example, any one of the internet-enabled devices 291a-296a of FIG. 2A.

Figure 7A:
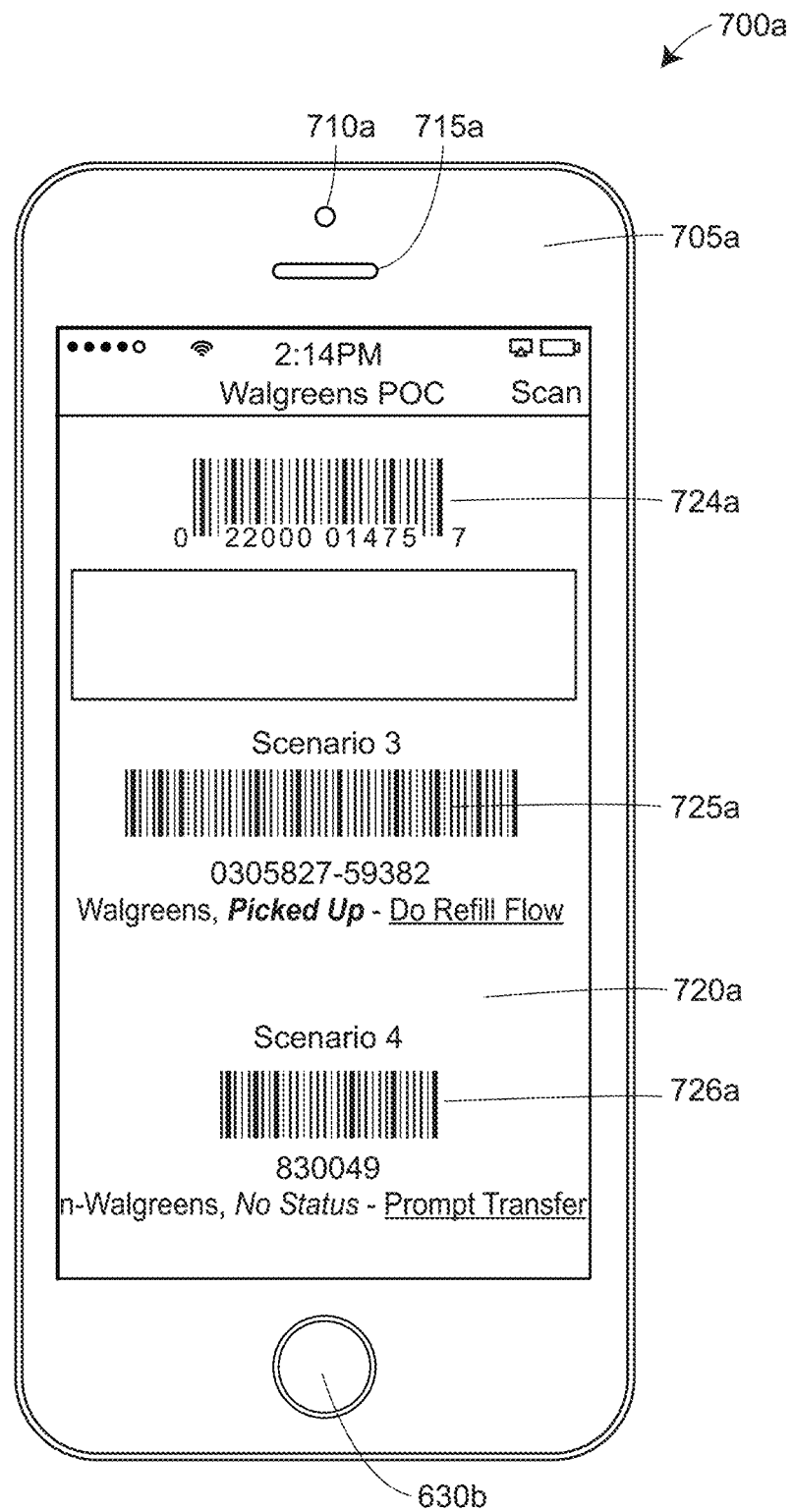
FIGS. 7A-7E depict an example system and associated devices with user interfaces for dynamic prescription status data access and transferring a prescription from a second pharmacy to a first pharmacy.

With reference to FIGS. 7A-7E, an example system 700b and associated devices with user interfaces 700a, 700c-e are depicted for dynamic prescription status data access and transferring a prescription from a second pharmacy to a first pharmacy. As illustrated in FIG. 7A, a dynamic prescription status information access system 700a may include a user device 705a having a camera 710a, a speaker 715a, a user interface display 720a, and a microphone 730a. The user interface display 720a may include a second barcode scan scenario (e.g., don't scan) 724a, a third barcode scan scenario (e.g., do refill flow) 725a, and a fourth barcode scan scenario 726a. The user device 705a may be similar to, for example, any one of the internet-enabled devices 291a-296a of FIG. 2A. As indicated in FIG. 7A with the outline rectangle, the third barcode scan scenario (e.g., do refill flow) 725a has been selected.

Figure 7B:
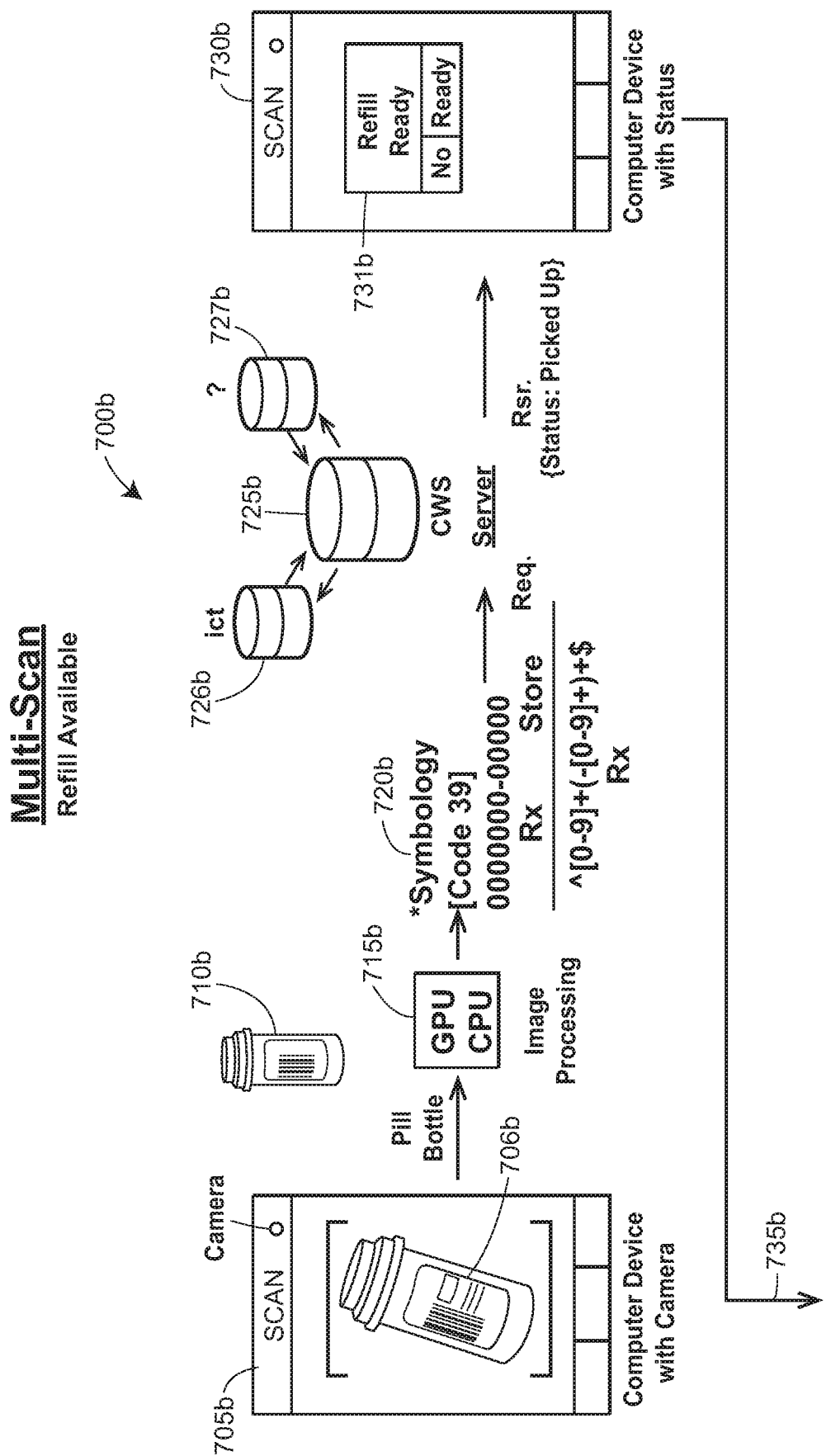

As depicted in FIG. 7B, the system may include a user device 705b having a user interface 706b for scanning a barcode representative of a prescription label number, or manually entering a prescription label number. For example, a barcode on a pill bottle 710b may be scanned and a graphical processing unit 715b may decode the barcode to generate prescription label data that is representative of a prescription label number. Symbology 720b may be associated with a prescription label number. Prescription status data may be automatically retrieved from any one of the databases 725b, 726b, 727b based on prescription label data. The user device 705b may automatically generate a user interface 730b having a prescription status message (e.g., refill ready) 731b based on, for example, the prescription status data, to initiate a prescription transfer flow 735b.

Figure 7C:
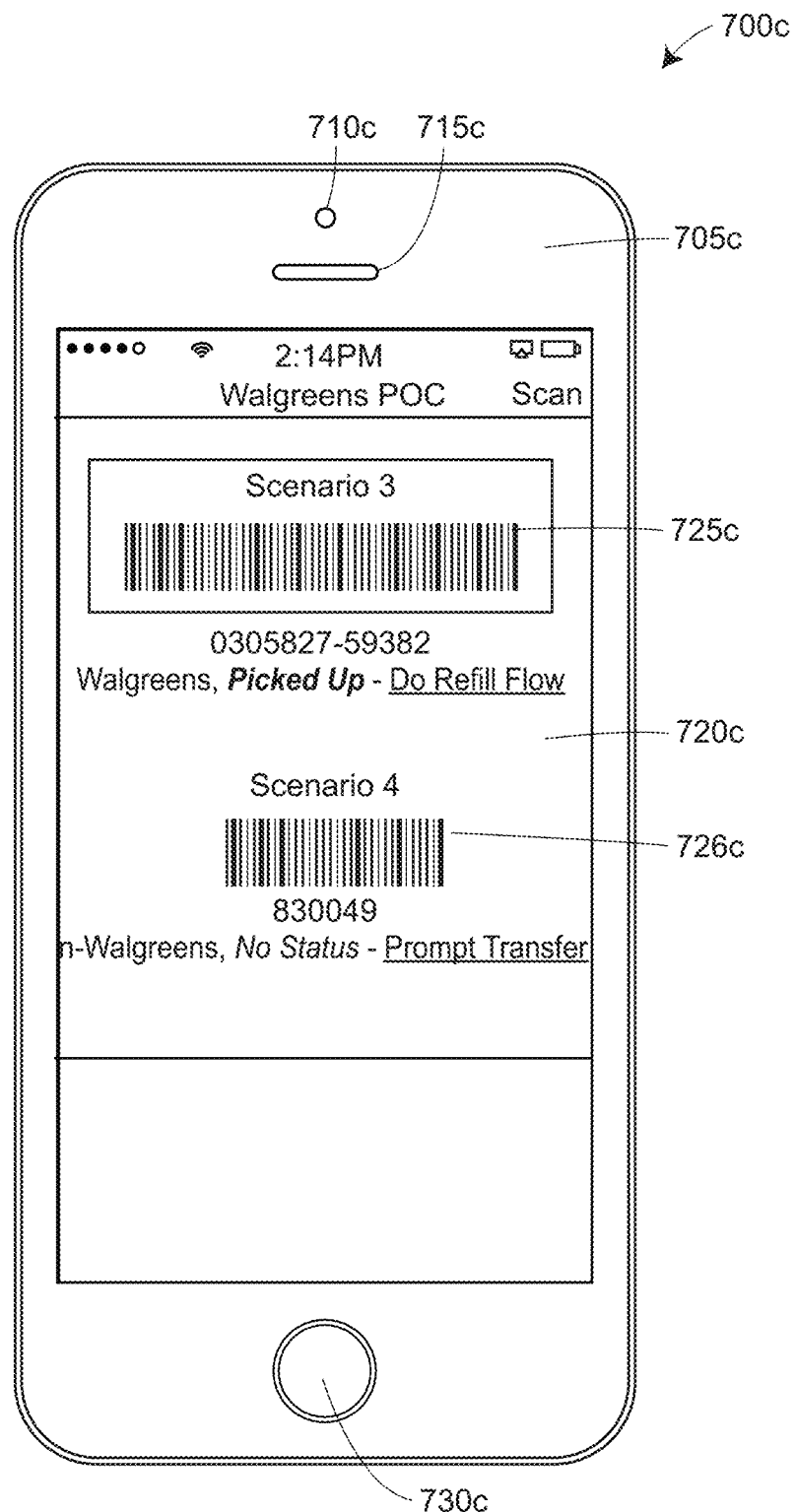

As illustrated in FIG. 7C, a dynamic prescription status information access system 700c may include a user device 705c having a camera 710c, a speaker 715c, a user interface display 720c, and a microphone 730c. The user interface display 720c may include a third barcode scan scenario (e.g., do refill flow) 725c and a fourth barcode scan scenario 726c. The user device 705c may be similar to, for example, any one of the internet-enabled devices 291a-296a of FIG. 2A. As indicated in FIG. 7C with the outline rectangle, the third barcode scan scenario (e.g., do refill flow) 725c has been selected.

Figure 7D:
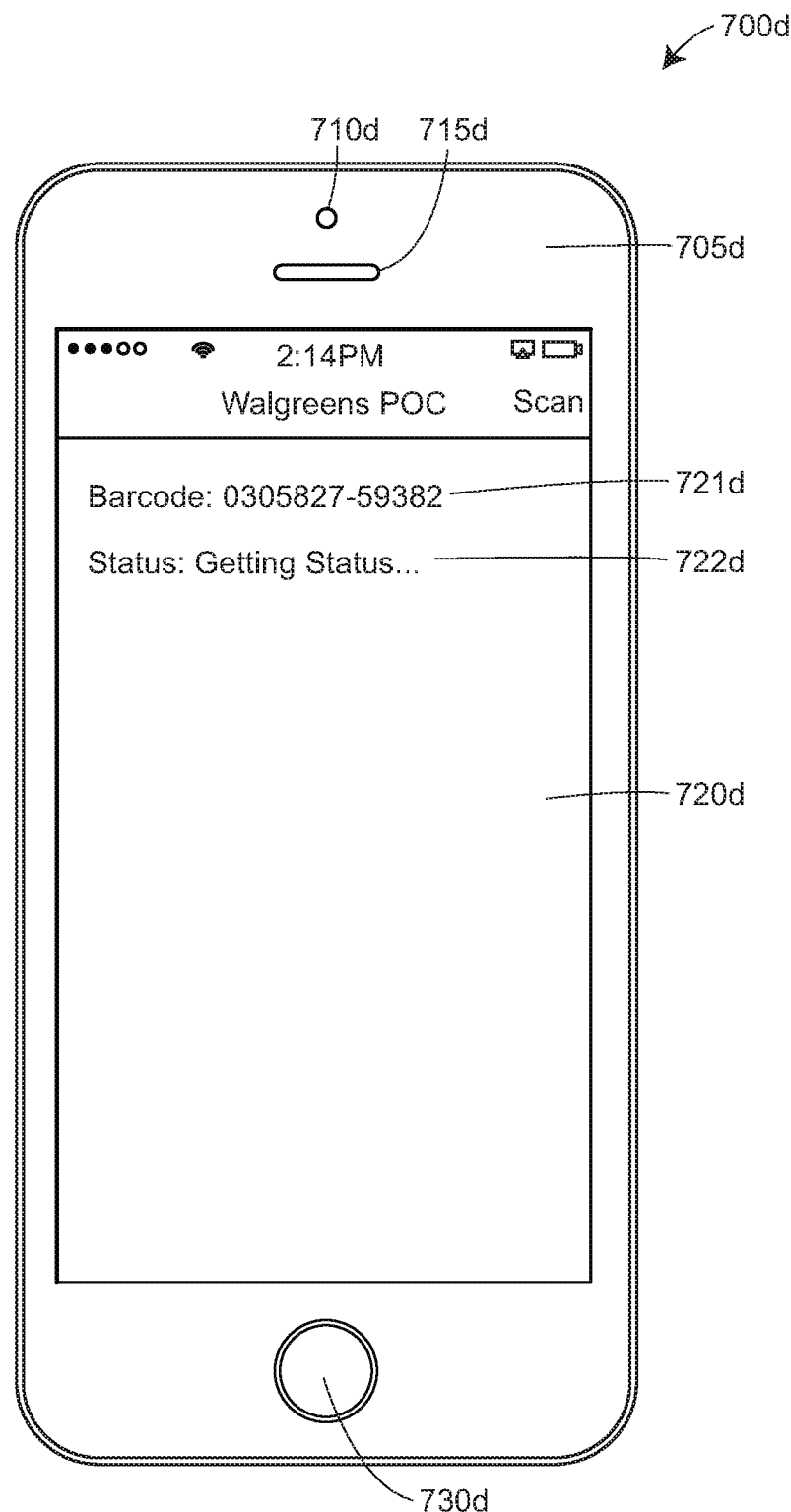
Figure 7E:
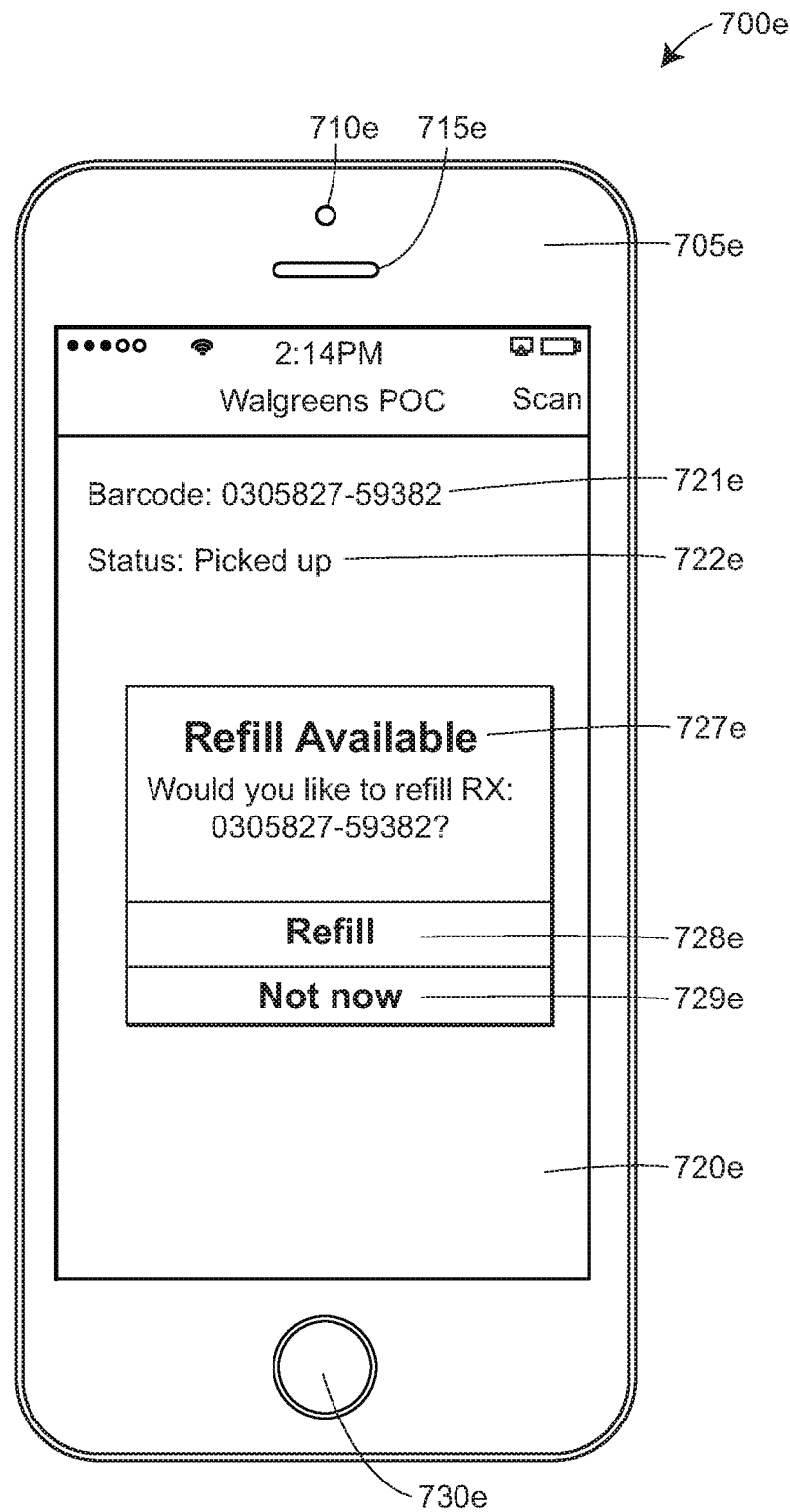

As illustrated in FIGS. 7D and 7E, a dynamic prescription status information access system 700d,e may include a user device 705d,e having a camera 710d,e a speaker 715d,e a user interface display 720d,e and a microphone 730d e. The user interface display 720d e may include a barcode scan instruction (e.g., a prescription label number) 721d,e, a prescription status message (e.g., getting status . . . , pick up) 722d, refill available information 727e, a Refill selection 728e, and a Not now selection 729e. The user device 705d,e may be similar to, for example, any one of the internet-enabled devices 291a-296a of FIG. 2A.

Figure 8A:
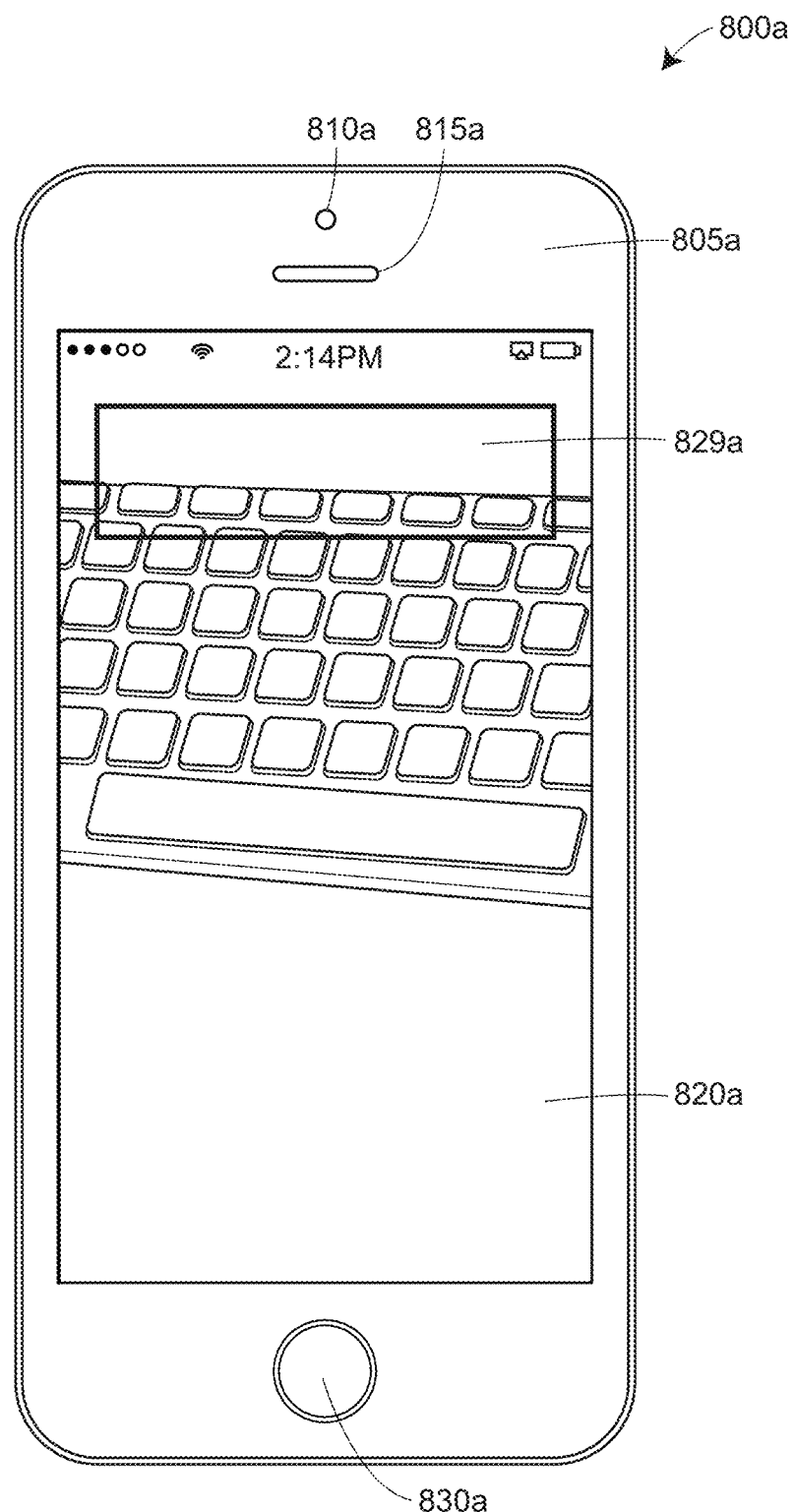
FIGS. 8A-8D depict example devices with user interfaces for dynamic prescription status data access and for refilling a prescription.

Turning to FIGS. 8A-8D, and with further reference to FIG. 6C, an example system 600c and example devices with user interfaces 800a-d are depicted for automatic prescription status data access and for refilling a prescription. As illustrated in FIG. 8A, a dynamic prescription status information access system 800a may include a user device 805a having a camera 810a, a speaker 815a, a user interface display 820a, and a microphone 830a. The user interface display 820a may include a keyboard entry user interface 829a. The user device 805a may be similar to, for example, any one of the internet-enabled devices 291a-296a of FIG. 2A.

Figure 8B:
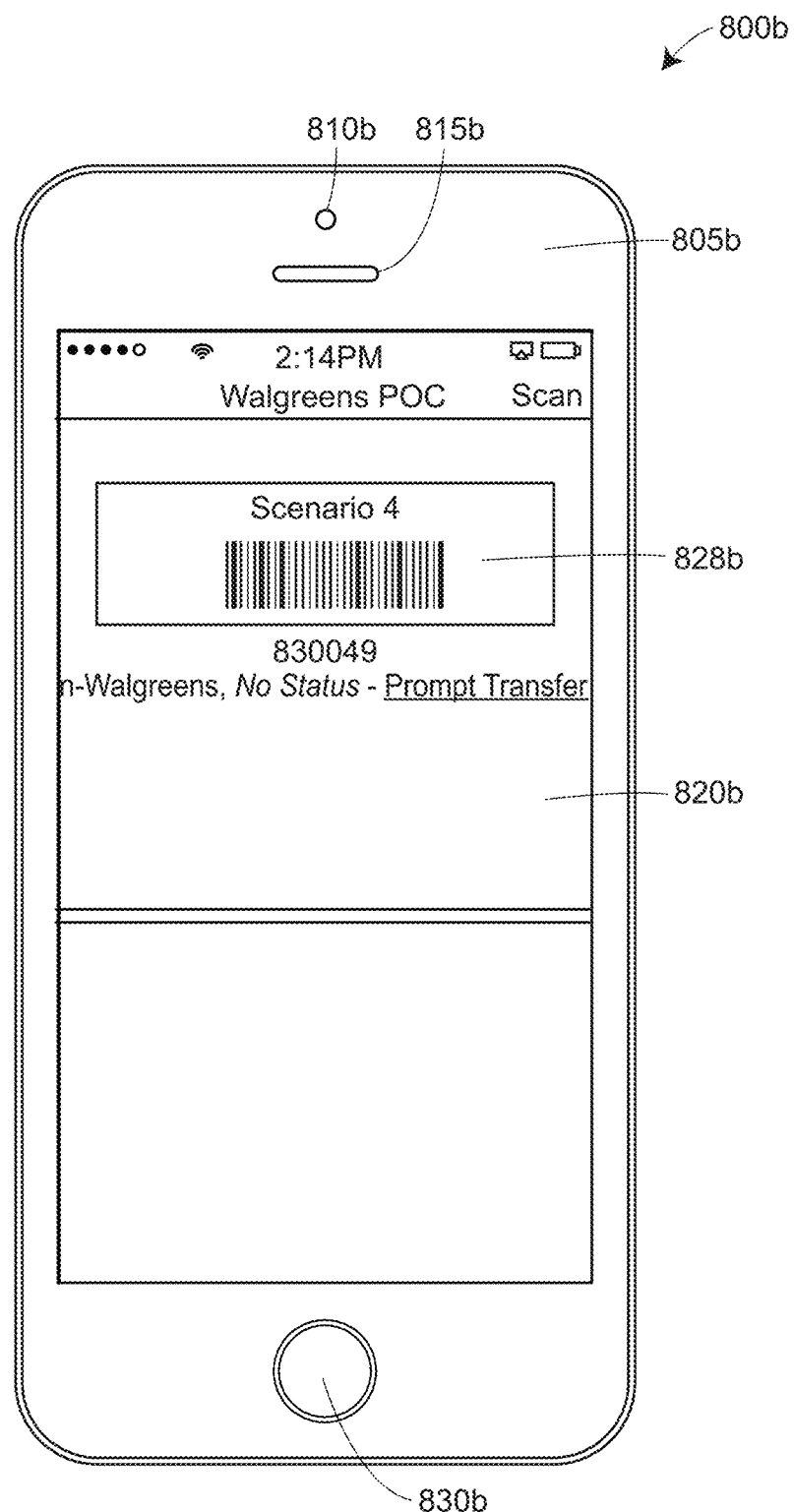

As illustrated in FIG. 8B, a dynamic prescription status information access system 800b may include a user device 805b having a camera 810b, a speaker 815b, a user interface display 820b, and a microphone 830b. The user interface display 820b may include a fourth barcode scan scenario (e.g., prompt transfer) 828b. The user device 805b may be similar to, for example, any one of the internet-enabled devices 291a-296a of FIG. 2A.

Figure 8C:
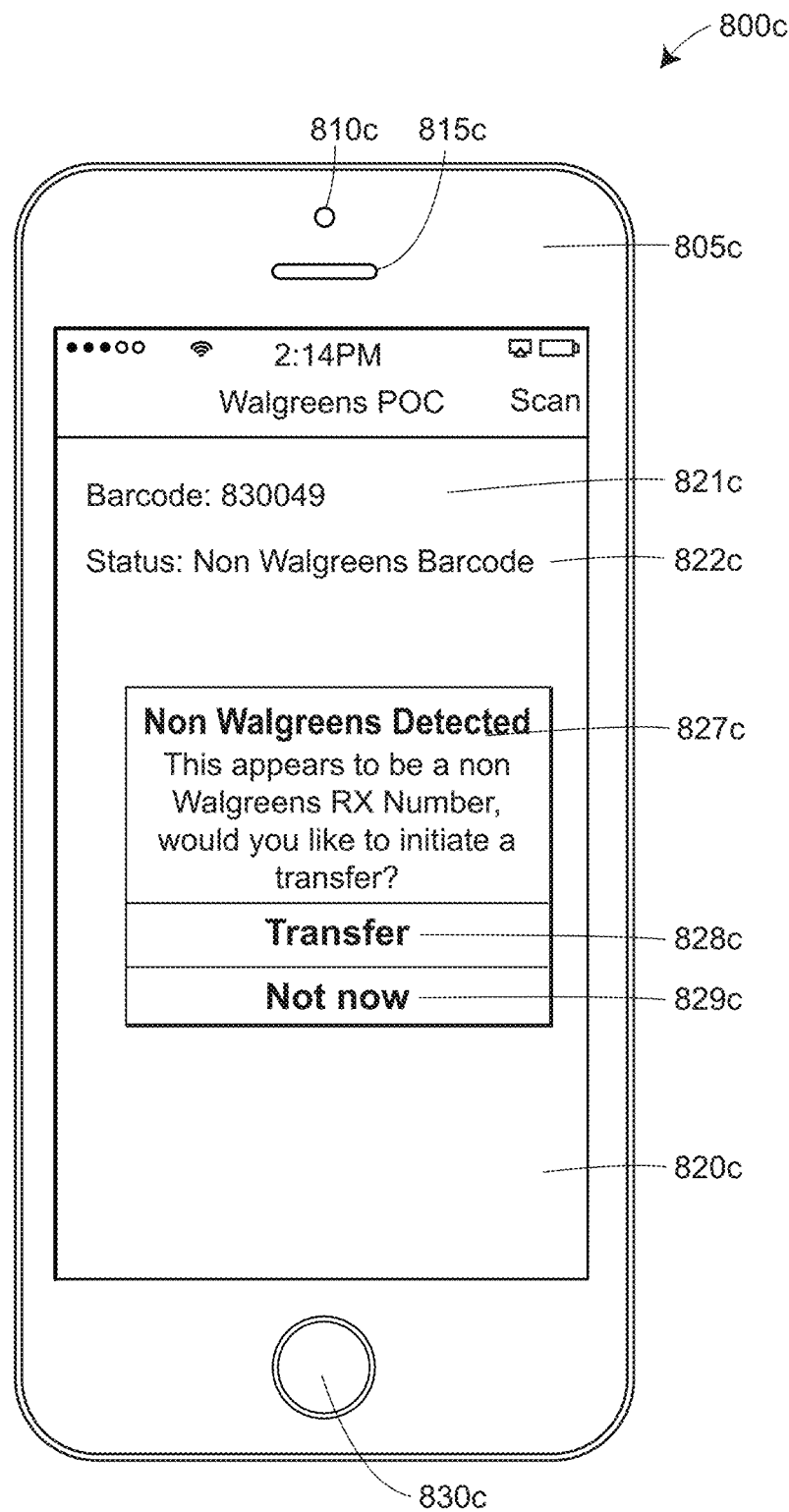

As illustrated in FIG. 8C, a dynamic prescription status information access system 800c may include a user device 805c having a camera 810c, a speaker 815c, a user interface display 820c, and a microphone 830c. The user interface display 820c may include a barcode scan instruction (e.g., a prescription label number) 821c, a prescription status message (e.g., Non-Walgreens barcode) 822c, and a Non Walgreens detected banner 827c having a prescription transfer selection icon 828c and a not now selection icon 829c. The user device 805c may be similar to, for example, any one of the internet-enabled devices 291a-296a of FIG. 2A.

Figure 8D:
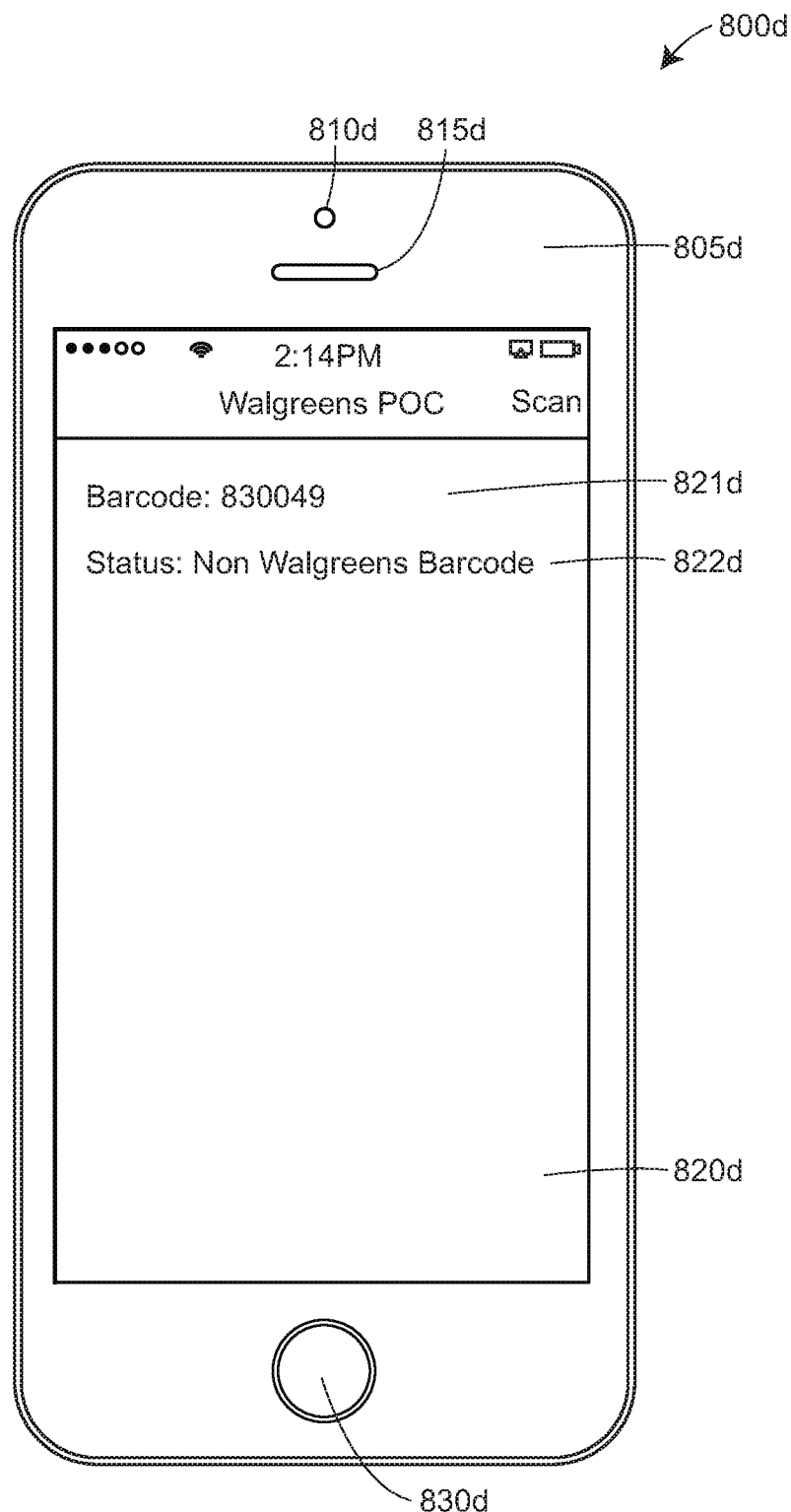

As illustrated in FIG. 8D, a dynamic prescription status information access system 800d may include a user device 805d having a camera 810d, a speaker 815d, a user interface display 820d, and a microphone 830d. The user interface display 820d may include a barcode scan instruction (e.g., a prescription label number) 821d and a prescription status message (e.g., Non Walgreens Barcode) 822d. The user device 805d may be similar to, for example, any one of the internet-enabled devices 291a-296a of FIG. 2A.

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A system for dynamically accessing prescription status data and automatically transferring a prescription to a desired pharmacy, the system comprising:

back-end components, physically located at a geographic location that is different than a geographic location of the desired pharmacy, having at least one database, wherein the at least one database includes: prescription information data, prescription label data, and prescription status data;

a user interface generation module stored on a memory of a user device that, when executed by a processor of the user device, causes the processor of the user device to generate a user interface on a display device of the user device, wherein the user interface includes: a barcode scan selection icon, a quick code scan selection icon, a user instruction information banner area, a general prescription status data information selection icon, a barcode number data entry area, and a prescription information selection icon;

a prescription information data receiving module stored on the memory of the user device that, when executed by the processor of the user device, causes the processor of the user device to receive prescription information data from the at least one database of the back-end components in response to a user selection of at least one of: the user instruction information banner area, the general prescription status data information selection icon, or the prescription information selection icon;

a prescription label data receiving module stored on the memory of the user device that, when executed by the processor of the user device, causes the processor of the user device to receive prescription label data from the at least one database of the back-end components in response to a user input via the user interface, wherein the user input includes at least one of: user selection of the barcode scan selection icon, user selection of the quick code scan selection icon, or user entry of barcode number data; and a prescription status data receiving module stored on the memory of the user device that, when executed by the processor of the user device, causes the processor of the user device to automatically receive prescription status data, from the at least one database of the back-end components, based on at least one of: the prescription label data or user selection of the general prescription status data information selection icon, wherein the prescription status data is representative of a status of a prescription and a first pharmacy that a user wants to fill the prescription;

when the status of the prescription is indicative of an existing prescription from the first pharmacy, and when the status of the prescription is indicative of a prescription that has not already been filled, the processor of the user device, further executing the user interface generation module, modifies the user interface to include a user prescription fill selection that allows a user to authorize the first pharmacy to fill the prescription, wherein, when the user selects the prescription fill selection, the prescription is automatically authorized to be filled by the first pharmacy;

when the status of the prescription is indicative of an existing prescription from a second pharmacy, and when the status of the prescription is indicative of a prescription that has not already been filled, the processor of the user device, further executing the user interface generation module, modifies the user interface to include a user prescription transfer selection that allows the user to authorize transfer of the prescription from the second pharmacy to the first pharmacy, wherein, when the user selects the prescription transfer selection, a prescription transfer request is automatically initiated to transfer the prescription from the second pharmacy to the first pharmacy; and when the status of the prescription is indicative of a prescription that has already been refilled, the processor of the user device, further executing the user interface generation module, modifies the user interface to include a message indicating that the prescription has already been refilled.

2. The system of claim 1, further comprising:
a prescription transfer data receiving module stored on a memory of a back-end computing device that, when executed by a processor of the back-end computing device, causes the processor of the back-end computing device to receive prescription transfer data in response to the prescription transfer request.

3. The system of claim 1, further comprising:
a barcode scanning module stored on the memory of the user device that, when executed by the processor of the user device, causes the processor of the user device to receive barcode data; and
a barcode data decoding module stored on the memory of the user device that, when executed by the processor of the user device, causes the processor of the user device to decode the barcode data, wherein the decoded barcode data includes the prescription label data.

4. The system of claim 1, further comprising:
a prescription status user interface module stored on a memory of a front-end device that, when executed by a processor of the front-end device, causes the processor of the front-end device to generate a prescription status user interface on a display device, wherein the prescription label data is manually entered by a user via the prescription status user interface.

5. The system of claim 3, wherein the barcode is representative of encoded prescription label number data using a symbology selected from: a one-dimensional linear barcode; a universal product code, a code 128, ITF-14, a prescription barcode, a two-dimensional matrix barcode, a quick response code, a data matrix, a MaxiCode, and an Aztec Code.

6. The system of claim 5, wherein the symbology incorporates a unique mapping between a message and a barcode.

7. The system of claim 6, wherein the unique mapping encodes at least one of: digits or characters of a message.

8. The system of claim 5, wherein the unique mapping encodes start and stop markers into a plurality of symbols selected from the group comprising: bars, rectangles, dots, hexagons, or spaces.

9. A method for dynamically accessing prescription status data and automatically transferring a prescription to a desired pharmacy, the method comprising:
providing back-end components, physically located at a geographic location that is different than a geographic location of the desired pharmacy, having at least one database, wherein the at least one database includes: prescription information data, prescription label data, and prescription status data;
generating a user interface on a display device of a user device in response to a processor of the user device executing a user interface generation module, wherein the user interface includes: a barcode scan selection icon, a quick code scan selection icon, a user instruction information banner area, a general prescription status data information selection icon, a barcode number data entry area, and a prescription information selection icon;
receiving prescription information data, at the processor of the user device from the at least one database of the back-end components, in response to a user selection of at least one of: the general prescription status data information selection icon or the prescription information selection icon;
receiving prescription label data, at the processor of the user device from the at least one database of the back-end components, in response to the processor of the user device executing a prescription label data receiving module, and further in response to receiving a user input via the user interface, wherein the user input includes at least one of: user selection of the barcode scan selection icon, user selection of the quick code scan selection icon, or user entry of barcode number data; and receiving prescription status data, at the processor of the user device from the at least one database of the back-end components, based on the prescription label data in response to the processor of the user device executing a prescription status data receiving module, wherein the prescription status data is representative of a status of a prescription and a first pharmacy that a user wants to fill the prescription;

when the status of the prescription is indicative of an existing prescription from the first pharmacy, and when the status of the prescription is indicative of a prescription that has not already been filled, the processor of the user device, further executing the user interface generation module, modifies the user interface to include a user prescription fill selection that allows a user to authorize the first pharmacy to fill the prescription, wherein, when the user selects the prescription fill selection, the prescription is automatically authorized to be filled by the first pharmacy;

when the status of the prescription is indicative of an existing prescription from a second pharmacy, and when the status of the prescription is indicative of a prescription that has not already been filled, the processor of the user device, further executing the user interface generation module, modifies the user interface to include a user prescription transfer selection that allows the user to authorize transfer of the prescription from the second pharmacy to the first pharmacy, wherein, when the user selects the prescription transfer selection, a prescription transfer request is automatically initiated to transfer the prescription from the second pharmacy to the first pharmacy; and when the status of the prescription is indicative of a prescription that has already been refilled, the processor of the user device, further executing the user interface generation module, modifies the user interface to include a message indicating that the prescription has already been refilled.

10. The method of claim 9, further comprising:
receiving prescription transfer data at the processor of the user device in response to the processor executing a prescription transfer data receiving module, and in response to the prescription transfer request.

11. The method of claim 9, further comprising:
receiving barcode data at the processor of the user device in response to the processor executing a barcode scanning module; and
decoding the barcode data in response to the processor of the user device executing a barcode data decoding module, wherein the decoded barcode data includes the prescription label data.

12. The method of claim 9, further comprising:
generating a prescription status user interface on a display device of the user device in response to the processor of the user device executing a prescription status user interface module, wherein the prescription label data is manually entered by a user via the prescription status user interface.

13. A non-transitory computer-readable medium storing instructions that, when executed by a processor of a computing device, cause the processor to dynamically access prescription status data, the non-transitory computer-readable medium comprising:

at least one database of back-end components that are physically located at a geographic location that is different than a geographic location of a desired pharmacy, wherein the at least one database includes: prescription information data, prescription label data, and prescription status data;

a user interface generation module that, when executed by the processor of the computing device, causes the processor to generate a user interface on a display device of the user device, wherein the user interface includes: a barcode scan selection icon, a user instruction information banner area, a barcode number data entry area, and a prescription information selection icon;

a prescription information data receiving module that, when executed by the processor of the computing device, causes the processor of the computing device to receive prescription information data from the at least one database of the back-end components in response to a user selection of at least one of: the user instruction information banner area or the prescription information selection icon;

a prescription label data receiving module that, when executed by the processor, causes the processor to receive prescription label data from the at least one database of the back-end components in response to a user input via the user interface, wherein the user input includes at least one of: user selection of the barcode scan selection icon or user entry of barcode number data; and a prescription status data receiving module that, when executed by the processor, causes the processor to automatically receive prescription status data from the at least one database of the back-end components, based on the prescription label data, wherein the prescription status data is representative of a status of a prescription and a first pharmacy that a user wants to fill the prescription;

when the status of the prescription is indicative of an existing prescription from the first pharmacy, and when the status of the prescription is indicative of a prescription that has not already been filled, the processor of the user device, further executing the user interface generation module, modifies the user interface to include a user prescription fill selection that allows a user to authorize the first pharmacy to fill the prescription, wherein, when the user selects the prescription fill selection, the prescription is automatically authorized to be filled by the first pharmacy;

when the status of the prescription is indicative of an existing prescription from a second pharmacy, and when the status of the prescription is indicative of a prescription that has not already been filled, the processor of the user device, further executing the user interface generation module, modifies the user interface to include a user prescription transfer selection that allows the user to authorize transfer of the prescription from the second pharmacy to the first pharmacy, wherein, when the user selects the prescription transfer selection, a prescription transfer request is automatically initiated to transfer the prescription from the second pharmacy to the first pharmacy; and when the status of the prescription is indicative of a prescription that has already been refilled, the processor of the user device, further executing the user interface generation module, modifies the user interface to include a message indicating that the prescription has already been refilled.

14. The non-transitory computer-readable medium of claim 13, further comprising:
 a prescription transfer data receiving module that, when executed by the processor, causes the processor to receive prescription transfer data in response to the prescription transfer request.

15. The system of claim 13, further comprising:
 a barcode scanning module that, when executed by the processor, causes the processor to receive barcode data; and
 a barcode data decoding module that, when executed by the processor, causes the processor to decode the barcode data, wherein the decoded barcode data includes the prescription label data.

16. The non-transitory computer-readable medium of claim 13, further comprising:
 a prescription status user interface module that, when executed by the processor, causes the processor to generate a prescription status user interface on a display device, wherein the prescription label data is manually entered by a user via the prescription status user interface.

17. The non-transitory computer-readable medium of claim 15, wherein the barcode is representative of encode prescription label number data using a symbology selected from: a one-dimensional linear barcode; a universal product code, a code 128, ITF-14, a prescription barcode, a two-dimensional matrix barcode, a quick response code, a data matrix, a MaxiCode, or an Aztec Code.

18. The non-transitory computer-readable medium of claim 17, wherein the symbology incorporates a unique mapping between a message and a barcode.

19. The non-transitory computer-readable medium of claim 18, wherein the unique mapping encodes at least one of: digits or characters of a message.

20. The non-transitory computer-readable medium of claim 17, wherein the unique mapping encodes start and stop markers into a plurality of symbols selected from the group comprising: bars, rectangles, dots, hexagons, or spaces.

* * * * *